(12) United States Patent
Kowalewski et al.

(10) Patent No.: US 12,138,054 B2
(45) Date of Patent: Nov. 12, 2024

(54) SPECIMEN COLLECTION DEVICE

(71) Applicant: PRP TECHNOLOGIES INC, Calgary (CA)

(72) Inventors: Ryszard Kowalewski, Calgary (CA); Marcin Kowalewski, Calgary (CA)

(73) Assignee: PRP TECHNOLOGIES INC, Calgary (CA)

( * ) Notice: Subject to any disclaimer, the term of this patent is extended or adjusted under 35 U.S.C. 154(b) by 0 days.

(21) Appl. No.: 18/038,586

(22) PCT Filed: Nov. 11, 2021

(86) PCT No.: PCT/US2021/058921
§ 371 (c)(1),
(2) Date: May 24, 2023

(87) PCT Pub. No.: WO2023/086090
PCT Pub. Date: May 19, 2023

(65) Prior Publication Data
US 2024/0293057 A1    Sep. 5, 2024

(51) Int. Cl.
*A61B 5/00*    (2006.01)
*A61B 5/15*    (2006.01)
*A61B 5/155*   (2006.01)

(52) U.S. Cl.
CPC ........ *A61B 5/155* (2013.01); *A61B 5/150221* (2013.01); *A61B 5/150351* (2013.01); *A61B 5/150755* (2013.01); *A61B 5/150992* (2013.01)

(58) Field of Classification Search
CPC .............. A61B 5/155; A61B 5/150221; A61B 5/150351; A61B 5/150755; A61B 5/150992
See application file for complete search history.

(56) References Cited

U.S. PATENT DOCUMENTS 3,734,079 A * 5/1973 Weber .............. A61B 5/150786
                                                600/370
4,111,199 A * 9/1978 Djerassi ................. A61B 5/153
                                                436/63

(Continued)

FOREIGN PATENT DOCUMENTS

WO    WO-2005087292 A1 *    9/2005    .............. A61M 5/00

*Primary Examiner* — May A Abouelela
(74) *Attorney, Agent, or Firm* — Jonathan D Feuchtwang

(57) ABSTRACT

A device for collecting blood, comprising: a tubular member having a diameter D1 enclosing an interior volume having a rated capacity, a distal end of the tubular member provided with a tip having a first through-hole in fluid communication with the interior volume, a proximal end of the tubular member provided a second through-hole in fluid communication with the interior volume; a cap formed of a self-healing material and configured to seal the tip of the tubular member; and a plunger movably accommodated within the interior volume of the tubular member, the plunger including an elongate member having an enlarged pad provided on a proximal end, an elastomeric member provided on a distal end and one or more locking wing members provided on and biased to extend away from the elongate member; wherein when the plunger is retracted to the rated capacity, the one or more locking wing members extend beyond the interior volume and engage with the proximal end of the tubular member.

29 Claims, 20 Drawing Sheets

(56) References Cited

U.S. PATENT DOCUMENTS

| | | | | |
|---|---|---|---|---|
| 4,645,486 A * | 2/1987 | Beal | A61B 5/15003 | 604/4.01 |
| 5,656,031 A * | 8/1997 | Thorne | A61M 5/322 | 604/110 |
| 9,326,914 B2 * | 5/2016 | Anitua Aldecoa | A61J 1/1406 | |
| 9,329,165 B2 * | 5/2016 | Ihm | G01N 33/491 | |
| 9,726,582 B2 * | 8/2017 | Rasmussen | G01N 1/28 | |
| 9,968,769 B2 * | 5/2018 | Sasayama | A61M 5/3202 | |
| 10,105,084 B2 * | 10/2018 | Chen | A61B 5/150351 | |
| 11,345,892 B2 * | 5/2022 | Larsen | A61B 5/153 | |
| 2002/0173733 A1 * | 11/2002 | Sarmiento | A61B 5/150732 | 604/218 |
| 2003/0120255 A1 * | 6/2003 | Odell | A61M 5/31525 | 134/8 |
| 2005/0065478 A1 * | 3/2005 | Alheidt | A61M 5/31511 | 604/218 |
| 2006/0030820 A1 * | 2/2006 | Alheidt | A61M 5/5013 | 604/537 |
| 2007/0232956 A1 * | 10/2007 | Harman | A61B 5/15194 | 600/573 |
| 2008/0097242 A1 * | 4/2008 | Cai | A61B 5/15003 | 600/578 |
| 2010/0025342 A1 * | 2/2010 | Morimoto | A61P 17/02 | 210/236 |
| 2012/0045826 A1 * | 2/2012 | Yantz | B01L 3/502715 | 422/69 |
| 2013/0011311 A1 * | 1/2013 | Kim | A61B 5/153 | 422/548 |
| 2013/0209985 A1 * | 8/2013 | Hoke | A61B 5/150755 | 435/307.1 |
| 2014/0128775 A1 * | 5/2014 | Andreae | A61B 5/153 | 600/581 |
| 2015/0209502 A1 * | 7/2015 | Bare | A61B 5/150755 | 604/506 |
| 2016/0279320 A1 * | 9/2016 | Zanin | B01D 21/262 | |
| 2017/0153165 A1 * | 6/2017 | Nwadigo | B01L 3/0231 | |
| 2017/0215781 A1 * | 8/2017 | Chen | A61B 5/150244 | |
| 2019/0313953 A1 * | 10/2019 | Kusters | G01N 21/31 | |
| 2020/0170558 A1 * | 6/2020 | Shin | A61B 5/150755 | |
| 2021/0147657 A1 * | 5/2021 | Matsutani | A61M 5/3202 | |
| 2021/0186391 A1 * | 6/2021 | Cho | A61B 5/150053 | |
| 2021/0267511 A1 * | 9/2021 | Chae | A61B 5/6833 | |
| 2021/0315498 A1 * | 10/2021 | Ivosevic | A61B 5/150267 | |
| 2021/0321921 A1 * | 10/2021 | Patel | A61B 5/150244 | |
| 2021/0361207 A1 * | 11/2021 | Rogers | A61B 5/150274 | |
| 2022/0054063 A1 * | 2/2022 | Samproni | A61B 5/150236 | |
| 2022/0110561 A1 * | 4/2022 | Blanchard | A61B 5/150992 | |
| 2022/0110562 A1 * | 4/2022 | Ma | A61B 5/150992 | |
| 2022/0175281 A1 * | 6/2022 | Chae | A61B 5/0002 | |
| 2023/0008783 A1 * | 1/2023 | Lykke | A61B 5/150992 | |
| 2023/0052321 A1 * | 2/2023 | Shaw | A61B 5/153 | |
| 2023/0088060 A1 * | 3/2023 | Chae | A61B 5/15111 | 600/365 |
| 2023/0166087 A1 * | 6/2023 | Teoh | A61M 25/0606 | 604/168.01 |
| 2023/0264185 A1 * | 8/2023 | Kim | A61B 5/150343 | 422/507 |
| 2024/0008782 A1 * | 1/2024 | Nsair | A61B 5/150755 | |
| 2024/0023853 A1 * | 1/2024 | Hu | A61B 5/150396 | |
| 2024/0138716 A1 * | 5/2024 | Chae | A61B 5/155 | |

* cited by examiner

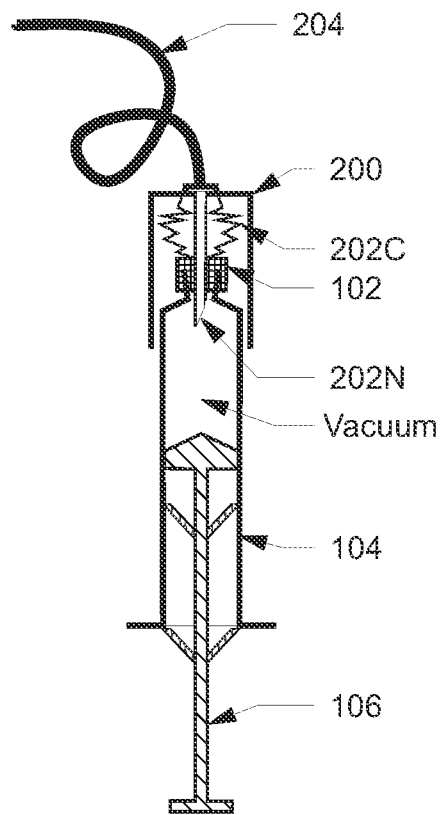
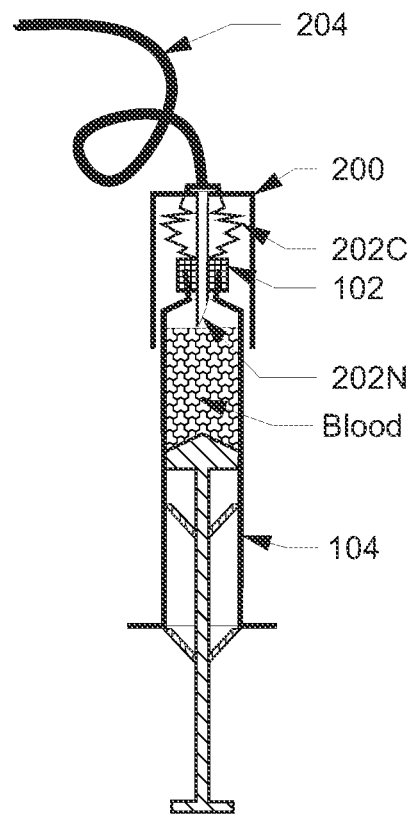
FIG. 40
FIG. 41

SPECIMEN COLLECTION DEVICE

BACKGROUND

Evacuated blood collection tubes are very easy to use, which is particularly appreciated when multiple samples of blood are being collected. Specimen samples are collected using a blood collection hub assembly featuring a multi-sampling safety valve which makes connection and disconnection of blood tubes very easy and convenient. The multi-sampling safety valve houses a needle inside an elastomeric cap or enclosure. The multi-sampling safety valve allows the blood flow into the blood collection tube upon connection of the blood collection tube with the hub. The multi-sampling safety valve automatically stops the blood flow upon removal of the tube. There is a wide selection of blood collection tubes for diagnostic use. However, most of such tubes are not FDA approved for collecting blood for subsequent injection of any of its components to the human body, as would be the case with autologous Platelet Rich Plasma for example. The blood collection tubes which are approved for such use are priced unreasonably high and require the use of syringes with needles for specimen withdrawal. Withdrawal of blood or plasma in this way exposes the performing physician to risks of being poked by the needle and also increases the risk of contaminating the specimen.

The use of blood collection tubes can be avoided when blood is drawn directly to a syringe. However, when multiple syringes of blood are drawn, a tubing with a clamp has to be used. The clamp is manually operated by the physician performing the procedure. The physician needs to clamp the tubing connected to the needle when inserting the needle to the patient's vein. The physician needs to connect a syringe for blood collection to the tubing and then remove the clamp from the line to enable flow to the syringe, before retracting the plunger. When the syringe is full of blood, the clamp needs to be re-applied, the syringe with blood disconnected and capped before being put away. The process needs to be repeated for every additional syringe of blood collected. Such a procedure is rather difficult to execute single-handedly by a physician or a nurse, without a risk of spillage of blood or contamination of components in communication with the blood.

Conventional syringes do not have the necessary features and geometry to engage with the hubs of the blood collection sets or kits that are equipped with multisampling safety valves.

The steps of blood collection and subsequent steps of separation of plasma can be very effectively simplified by a specially designed syringe-like device which can connect to the popular Tube Holder hubs with multisampling safety valves. Coincidentally, such a design can also facilitate transfer of blood-derived liquid fractions to other syringes directly without the need for additional connectors or needles. A novel solution to improve the overall platelet rich plasma (PRP) preparation process and reduce the risks to both the physician and the patient is presented herein.

BRIEF DESCRIPTION OF THE DRAWINGS

FIG. 11 shows the device 100 of FIG. 10 prior to being fluidically coupled to a syringe 300;

FIG. 13 shows the device 100 of FIG. 12 after plasma and buffy coat have been transferred to the syringe 300;

FIG. 40 shows the device 100 of FIG. 39 fluidically coupled with blood collection hub assembly 200;

FIG. 41 shows the device 100 of FIG. 40 fluidically coupled with blood collection hub assembly 200 after a specimen of blood has been drawn into the interior volume 104L by the partial vacuum;

SUMMARY OF THE INVENTION

Figure 1:
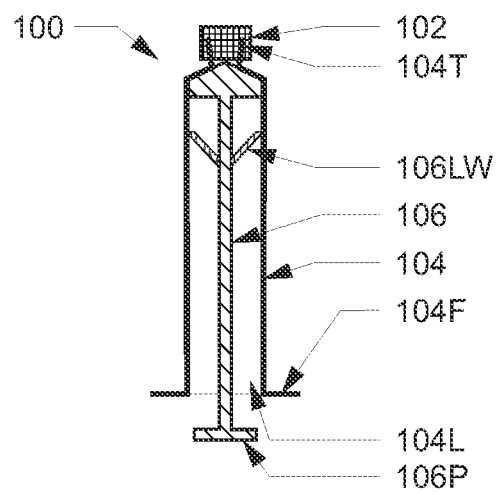
FIG. 1 depicts an example of a syringe-like device 100 according to the present invention.

Example 1: A method for collecting a blood specimen from a patient, comprising the steps of:
providing a first syringe-like device including:
  a tubular member having a diameter D1 enclosing an interior volume, a distal end of the tubular member provided with a tip having a first through-hole in fluid communication with the interior volume, a proximal end of the tubular member having a second through-hole in fluid communication with the interior volume;
  a plunger movably accommodated within the interior volume of the tubular member, the plunger including an elongate member having an enlarged pad provided on a proximal end, an elastomeric member provided on distal end and one or more locking wing members provided on and biased to extend away from the elongate member;
providing a first cap at least partially formed of a pierceable, self-healing material;
providing a blood collection hub assembly including:
  tubing having a first end in fluid communication with a first hollow needle in a vein of a patient and a second end in fluid communication with a second hollow needle;
  a multisampling safety valve which includes the second hollow needle fully enclosed by a second cap which extends beyond the sharpened tip of the second hollow needle, where the second cap is at least partially formed of a flexible, pierceable, self-healing material which is biased to return to its fully extended shape in the absence of an external force;
  wherein the multisampling safety valve is closed when the second cap is fully extended and the second hollow needle is enclosed within the second cap, and the multisampling safety valve is open when the second cap is at least partially collapsed such that the second hollow needle pierces through the second cap; and
  a wall encircling the second hollow needle and second cap and having a diameter D2 slightly larger than D1 and configured to align an axis of the second hollow needle with an axis of the first through-hole when the blood collection hub assembly is placed in engagement with the tubular member;
  placing the first cap on the tip of the tubular member with plunger fully inserted into the tubular member such that the distal end of the plunger is proximate the distal end of the tubular member;
  retracting the plunger proximally thereby creating a partial vacuum within the interior volume of the tubular member; and
  placing the blood collection hub assembly in engagement with the capped tip of the tubular member of the syringe-like device such that the second hollow needle pierces the second cap and the first cap and extends into the first through-hole;
wherein the specimen of blood is drawn from the patient, through the first hollow needle, the tubing; the second hollow needle, into the interior volume of the tubular member of the syringe-like device by the partial vacuum within the interior volume of the tubular member.

Example 2: The method of Example 1, comprising:
disengaging the blood collection hub assembly from the first syringe-like device;
clipping a proximal portion of tubular member and a proximal portion of the plunger of the first syringe-like device; and
centrifuging the first syringe-like device to separate the blood specimen into plasma, buffy coat and red blood cells (RBC).

Example 3: The method of Example 2, comprising:
providing a first conventional syringe having an at least partially inserted plunger;
removing the first cap from the tip of the first syringe-like device;
fluidically coupling a tip of the first conventional syringe with the tip of the first syringe-like device and transferring the plasma and the buffy coat into the first conventional syringe;
disconnecting the first conventional syringe from the first syringe-like device; and
either emptying or discarding the first syringe-like device.

Example 4: The method of Example 3, comprising;
providing a second syringe-like device with the first cap removed;
fluidically coupling the tip of the first conventional syringe with the tip of the second syringe-like device and transferring the plasma and buffy coat into the second syringe-like device;
disconnecting the first conventional syringe from the second syringe-like device;
setting aside the first conventional syringe;
placing the first cap on the tip of the second syringe-like device;
clipping a proximal portion of tubular member and a proximal portion of the plunger of the second syringe-like device; and
centrifuging the second syringe-like device to yield a layer of platelets and a layer of platelet poor plasma.

Example 5: The method of Example 4, comprising:
providing a second conventional syringe or reusing the first conventional syringe;
removing the first cap from the tip of the second syringe-like device;
fluidically coupling the tip of the first or second conventional syringe with the tip of the second syringe-like device and transferring a portion of the platelet poor plasma into the first or second conventional syringe;
disconnecting the first or second conventional syringe from the second syringe-like device; and
setting aside the first or second conventional syringe.

Example 6: The method of Example 5, comprising:
providing a third conventional syringe or reusing the first or second conventional syringe by first emptying the contents, if any, from the first or second conventional syringe; and fluidically coupling the tip of the first, second, or third conventional syringe with the tip of the second syringe-like device and transferring the precipitated platelets with platelet-poor plasma into the first, second, or third conventional syringe.

Example 7: A device for collecting blood, comprising:
a tubular member having a diameter D1 enclosing an interior volume having a rated capacity, a distal end of the tubular member provided with a tip having a first through-hole in fluid communication with the interior volume, a proximal end of the tubular member provided a second through-hole in fluid communication with the interior volume;
a cap at least partially formed of a pierceable, self-healing material and configured to seal the tip of the tubular member; and
 a plunger movably accommodated within the interior volume of the tubular member, the plunger including an elongate member having an enlarged pad provided on a proximal end, an elastomeric member provided on a distal end and one or more locking wing members provided on and biased to extend away from the elongate member;
 wherein when the plunger is retracted to the rated capacity, the one or more locking wing members extend beyond the interior volume and engage with the proximal end of the tubular member.

Example 8: The device of Example 7, wherein the one or more locking wing members provide haptic feedback when they engage with the proximal end of the tubular member.

Example 9: The device of Example 7, wherein the one or more locking wing members provide an audible sound when they engage with the proximal end of the tubular member.

Example 10: The device of Example 7, wherein the cap includes a plug which engages and seals the first through-hole.

Example 11: The device of Example 7, wherein if the cap is placed in engagement with the tip of the tubular member after the plunger is at least partially inserted into the tubular member, and then the plunger is retracted, a partial vacuum is created within the interior volume of the tubular member.

Example 12: The device of Example 7 wherein the one or more locking wing members comprise a first set of locking wing members provided a distance X1 from the proximal end of elongate member and a second set of locking wing members provided a distance X2 from the proximal end of elongate member wherein X1<X2.

Example 13: The device of Example 12, wherein the distance X1 and X2 each corresponds to the interior volume defined or obtained by the position of the plunger within the tubular member; and
 wherein X1 and X2 each define a trigger point at which each set of locking wing members will lock the plunger.

Example 14: The device of Example 7, wherein the capped tip of the tubular member is configured to sealingly engage and fluidically connect with a needle of a multisampling safety valve of a blood collection hub assembly.

Example 15: The device of Example 14, wherein the cap and the tip of the tubular member are configured to operatively engage with a valve of the multisampling safety valve.

Example 16: The device of Example 15, wherein the blood collection hub assembly includes a circular wall having a diameter which is sized to accommodate a distal end of the tubular member, and wherein an interaction between the circular wall and the distal end of the tubular member orients the needle with respect to the cap to facilitate insertion of the needle through the cap.

Example 17: A method for collecting a blood specimen from a patient into a syringe-like device, comprising the steps of:
providing a syringe-like device including:
 a tubular member having a diameter D1 enclosing an interior volume, a distal end of the tubular member provided with a tip having a first through-hole in fluid communication with the interior volume, a proximal end of the tubular member provided a second through-hole in fluid communication with the interior volume;
 a plunger movably accommodated within the interior volume of the tubular member, the plunger including an elongate member having an enlarged pad provided on a proximal end, an elastomeric member provided on distal end and one or more locking wing members provided on and biased to extend away from the elongate member;
providing a first cap at least partially formed of a pierceable, self-healing material;
providing a blood collection hub assembly including:
 tubing having a first end in fluid communication with a first hollow needle in a vein of a patient and a second end in fluid communication with a second hollow needle;
a multisampling safety valve which includes the second hollow needle fully enclosed by a second cap which extends beyond the sharpened tip of the second hollow needle, where the second cap is at least partially formed of a flexible, pierceable, self-healing material which is biased to return to its fully extended shape in the absence of an external force;
wherein the multisampling safety valve is closed when the second cap is fully extended and the needle is enclosed within the second cap, and the multisampling safety valve is open when the second cap is at least partially collapsed such that the second hollow needle pierces through the second cap; and
 a wall encircling the second hollow needle and the second cap, the wall having a diameter D2 slightly larger than D1 and configured to align an axis of the second hollow needle with an axis of the first through-hole when the blood collection hub assembly is placed in engagement with the tubular member;
 placing the first cap on the tip of the tubular member with plunger fully inserted into the tubular member such that the distal end of the plunger is proximate the distal end of the tubular member;
 placing the blood collection hub assembly in engagement with the capped tip of the tubular member of the syringe-like device such that the second hollow needle pierces the second cap and the first cap and extends into the first through-hole; and
 retracting the plunger proximally thereby drawing a specimen of blood from the patient, through the first hollow needle, the tubing; the second hollow needle, into the interior volume of the tubular member of the syringe-like device by the partial vacuum within the interior volume of the tubular member.

Example 18: The method of Example 17, comprising:
disengaging the blood collection hub assembly from the syringe-like device;
clipping a proximal portion of tubular member and a proximal portion of the plunger of the syringe-like device; and centrifuging the syringe-like device to separate the blood specimen into plasma, buffy coat and red blood cells (RBC);

Example 19: The method of Example 18, comprising:
providing a conventional syringe having an at least partially inserted plunger;
removing the cap from the tip of the syringe-like device;
fluidically coupling a tip of the conventional syringe with the tip of the syringe-like device and transferring the plasma and the buffy coat into the conventional syringe;
disconnecting the conventional syringe from the syringe-like device; and
either emptying the syringe-like device or discarding the syringe-like device;

Example 20: The method of Example 19, comprising;
providing an empty syringe-like device with the cap removed from the tip thereof;
fluidically coupling the tip of the conventional syringe with the tip of the syringe-like device and transferring the plasma and buffy coat into the syringe-like device;
disconnecting the conventional syringe from the syringe-like device;
setting aside the conventional syringe;
placing a cap on the tip of the syringe-like device;
clipping a proximal portion of tubular member and a proximal portion of the plunger of the syringe-like device; and
centrifuging the syringe-like device to yield a layer of platelets and a layer of platelet poor plasma.

Example 21: The method of Example 20, comprising:
providing an empty conventional syringe;
removing the cap from the tip of the syringe-like device;
fluidically coupling the tip of the conventional syringe with the tip of the syringe-like device and transferring a portion of the platelet poor plasma into the conventional syringe;
disconnecting the conventional syringe from the syringe-like device; and
discarding or emptying the conventional syringe;

Example 22: The method of Example 21, comprising:
providing an empty conventional syringe;
fluidically coupling the tip of the conventional syringe with the tip of the syringe-like device and transferring the precipitated platelets with platelet-poor plasma into the conventional syringe;
disconnecting the conventional syringe from the syringe-like device.

Example 23: The method of Example 2, comprising:
providing a second syringe-like device with the first cap removed, and having an at least partially inserted plunger;
removing the first cap from the tip of the first syringe-like device;
fluidically coupling a tip of the second syringe-like device with the tip of the first syringe-like device using an adapter and transferring the plasma and the buffy coat into the second syringe-like device;
disconnecting the second syringe-like device from the first syringe-like device; and
discarding the first syringe-like device.

Example 24: The method of Example 23, comprising;
removing the adapter from the tip of the second syringe-like device;
placing the first cap on the tip of the second syringe-like device;
clipping a proximal portion of tubular member and a proximal portion of the plunger of the second syringe-like device; and
centrifuging the second syringe-like device to yield a layer of platelets and a layer of platelet poor plasma.

Example 25: The method of Example 24, comprising:
providing a third syringe-like device with the first cap removed;
removing the first cap from the second syringe-like device;
fluidically coupling the tip of the third syringe-like device with the tip of the second syringe-like device using the adapter, and transferring a portion of the platelet poor plasma into the third syringe-like device;
disconnecting the third syringe-like device and the adapter from the second syringe-like device; and
discarding the third syringe-like device.

Example 26: The method of Example 25, comprising:
providing an empty conventional syringe; and
fluidically coupling the tip of the conventional syringe with the tip of the second syringe-like device and transferring the precipitated platelets with platelet-poor plasma into the conventional syringe.

Example 27: A method for collecting a blood specimen from a patient, comprising the steps of:
providing a first syringe-like device including:
a tubular member having a diameter D1 enclosing an interior volume, a distal end of the tubular member provided with a tip having a first through-hole in fluid communication with the interior volume, a proximal end of the tubular member having a second through-hole in fluid communication with the interior volume;
a plunger movably accommodated within the interior volume of the tubular member, the plunger including an elongate member having an enlarged pad provided on a proximal end, an elastomeric member provided on distal end;
providing a first cap at least partially formed of a pierceable, self-healing material;
providing a blood collection hub assembly including:
tubing having a first end in fluid communication with a first hollow needle in a vein of a patient and a second end in fluid communication with a second hollow needle;
a multisampling safety valve which includes the second hollow needle, wherein the multisampling safety valve is closed when the second needle is disengaged from the first cap, and the multisampling safety valve is open when the second hollow needle is engaged with the first cap;
placing the first cap on the tip of the tubular member with plunger fully inserted into the tubular member such that the distal end of the plunger is proximate the distal end of the tubular member; and
placing the blood collection hub assembly in engagement with the capped tip of the tubular member of the syringe-like device such that the second hollow needle pierces the first cap and extends into the first through-hole.

Example 28: The method of Example 27, further comprising:
providing means for selectively preventing the plunger from advancing into the tubular member;
wherein prior to or after the step of placing the blood collection hub assembly in engagement with the capped tip of the tubular member of the syringe-like device, retracting the plunger proximally thereby creating a partial vacuum within the interior volume of the tubular member;

engaging said means for selectively preventing the plunger from advancing into the tubular member; wherein the specimen of blood is drawn from the patient, through the first hollow needle, the tubing; the second hollow needle, into the interior volume of the tubular member of the syringe-like device by the partial vacuum within the interior volume of the tubular member.

DETAILED DESCRIPTION

FIG. 1 depicts an exemplary syringe-like device 100 having a pierceable rubber-like cap 102 at least partially formed of an elastomeric, self-healing material. Device 100 includes a tubular member 104 having an interior volume in fluid communication with a lumen or through-hole 104L extending along its length. A proximal end of the tubular member 104 is provided with a flange 104F which surrounds and extends away from the exterior surface of the tubular member 104. A plunger 106 is movably housed within the lumen 104L. A proximal end of the plunger 106 may be equipped with an enlarged pad 106P for advancing or retracting the plunger with fingers or the like. According to FIG. 2-3, a distal end of the plunger may be provided with an elastomeric member 106E. The plunger 106 may be provided with one or more locking wing members 106LW which are biased to extend away from the plunger 106. In the examples depicted in the drawings two locking wing members are illustrated; however, a single locking wing member 106LW may suffice. The locking wing members 106LW are constrained by the internal surface of the tubular member 104. When the plunger 106 is withdrawn to its rated capacity, the locking wing members 106LW extend beyond the interior volume of the tubular member, i.e., are no longer constrained by the internal surface of the tubular member 104, pop-out from the tubular member 104 and engage with the proximal end of the tubular member 104 thereby preventing or inhibiting the advancement of the plunger in a distal direction. The locking wing members 106LW provide haptic feedback when they pop-out from the tubular member 104 and engage with the proximal end of the tubular member 104. Namely, there is a slight vibration and sound made by the locking wing members 106LW. This haptic feedback alerts the user that the rated capacity of the syringe-like device has been achieved without the need for a visual inspection.

Figures 2, 3:
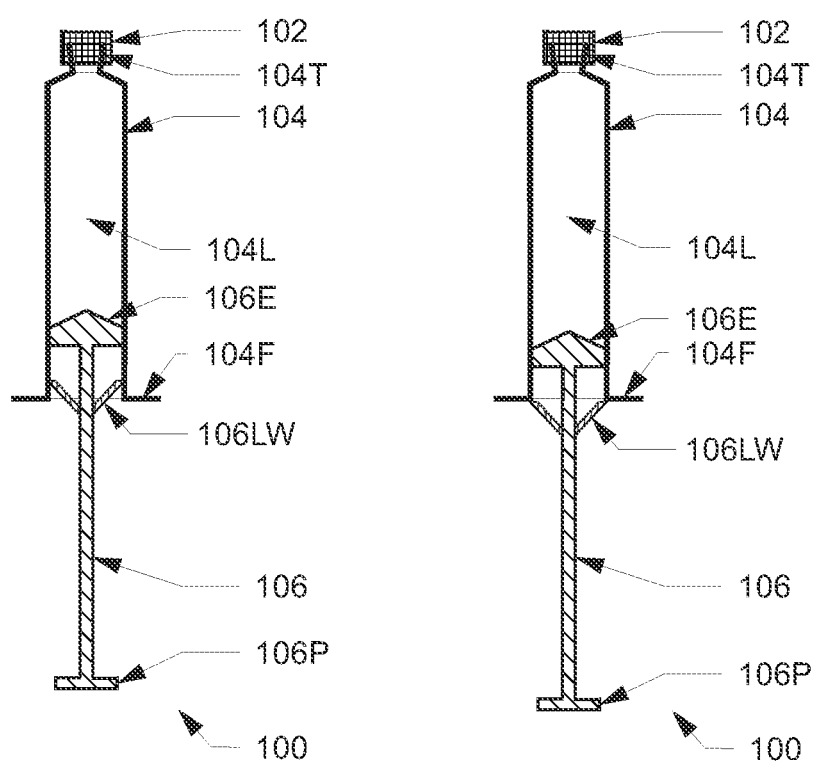
FIGS. 2-3 show the device 100 of FIG. 1 just prior to and after the locking wing members lock.

In the example device shown in FIG. 1, if the plunger 106 is retracted from a fully inserted position with the cap 102 sealingly engaged with a distal end of the tubular member 104 (See, FIGS. 2 and 3), then a partial vacuum is created within the interior volume 104L. FIG. 2 depicts the plunger partially retracted such that the locking wing members 106LW are still housed within the tubular member 104 and remain unlatched and FIG. 3 depicts the plunger retracted to the rated capacity with the locking wing members 106LW extending outside of the tubular member 104 and engaged (latched) with the proximal end of the tubular member 104. According to one aspect of the invention, the device 100 provides haptic (audible click plus slight vibration) feedback when the locking wing members 106LW engage (latch) with the proximal end of the tubular member 104.

The cap 102 may be at least partially formed of or include a pierceable, self-healing material (e.g., elastomeric material) which is configured to be pierced by the hollow needle 202N of the multisampling safety valve 202 of the blood collection hub assembly 200. In some examples, the cap 102 is actually a plug which fits into and seals a first through-hole in a tip 104T of the tubular member. In other examples, the cap 102 includes a plug portion as well as a portion which engages with an external surface of the tip 104T. In other examples the cap 102 may not include the plug and only engage the external surface of the tip 104T.

Figure 4:
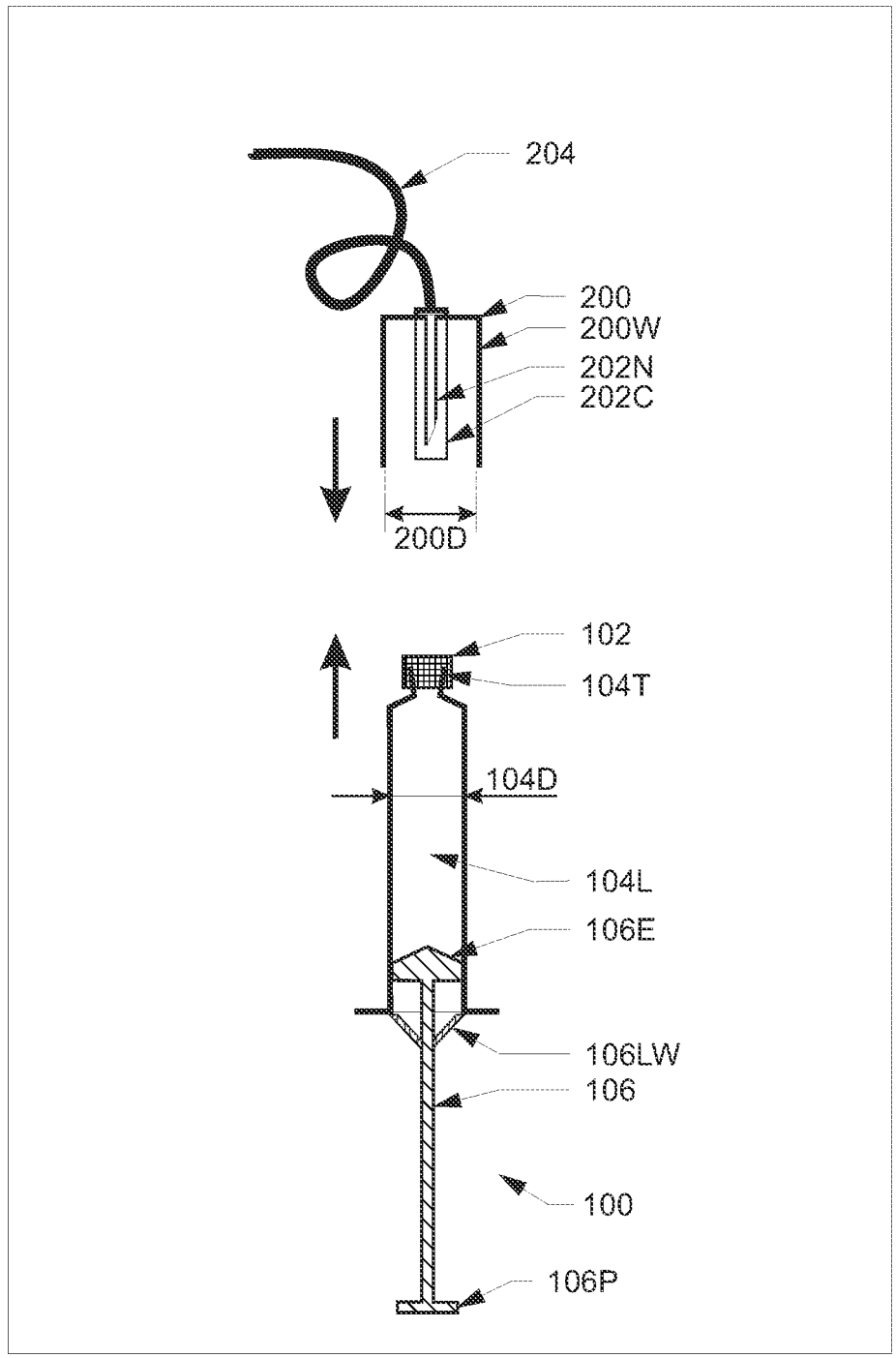
FIGS. 4-6 show the device 100 of FIG. 1 prior to being engaged with a blood collection hub assembly 200, after being engaged with the blood collection hub, and after a specimen of blood is collected.

FIG. 4 shows a device 100 with a partial vacuum within the volume 104L. The hollow needle 202N has a lumen in fluid communication with the blood collection tubing 204. The multisampling safety valve 202 includes a hollow needle 202N fully enclosed by a cap or enclosure 202C which extends beyond the sharpened tip of the needle 202N. Cap 202C is at least partially formed of a flexible, pierceable, self-healing material which is biased to return to its fully extended shape in the absence of an external force. Cap 202C forms part of the valve 202 such that the valve 202 is closed when the cap 202C is fully extended and the needle 202N is enclosed within the cap 202C; and the valve 202 is open when the cap 202C is at least partially collapsed such that the needle 202N pierces through the cap 202C. The cap 102 serves as a gas/liquid barrier before being pierced by the needle 202N of the multi-sampling safety valve 202 and after multiple insertions and removal of the needle 202N from the cap 102.

As shown in FIG. 4, the tubular member 104 has external diameter 104D slightly smaller than the internal diameter 200D of the blood collection hub assembly 200. In the Example depicted in FIG. 4, the syringe-like device 100 is provided with a female tip 104T with a lumen (first through-hole) at a distal end thereof. When the blood collection hub assembly 200 is brought into engagement with the first cap 102 of the device 100, the hollow needle 202N pierces the cap 102 and extends into the lumen of the female tip 104T.

Method of Use

A method for using the device 100 in the preparation of platelet rich plasma will now be explained with reference to FIGS. 5-9.

Figure 5:
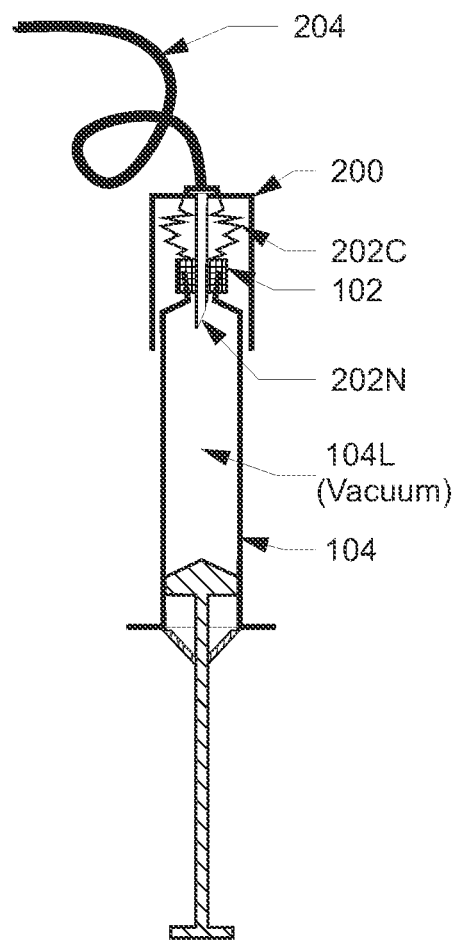
Figure 6:
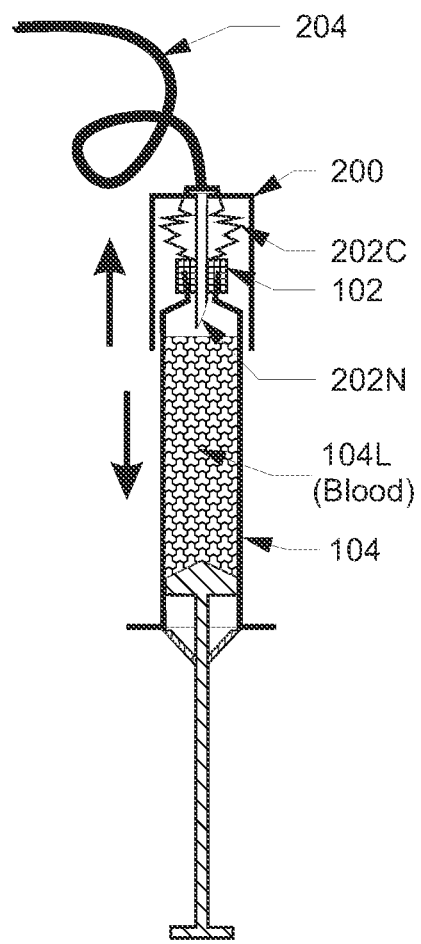

In FIG. 5 hub assembly 200 is placed in engagement with device 100 with a partial vacuum within the interior volume 104L. Hollow needle 202N has pierced the cap 202C and cap 102 thereby placing the lumen of needle 202N in fluid communication with the interior volume 104L of the syringe-like member 100. As shown in FIG. 6, the partial vacuum pulls blood through the tubing 204 and into the interior volume 104L.

Figure 7:
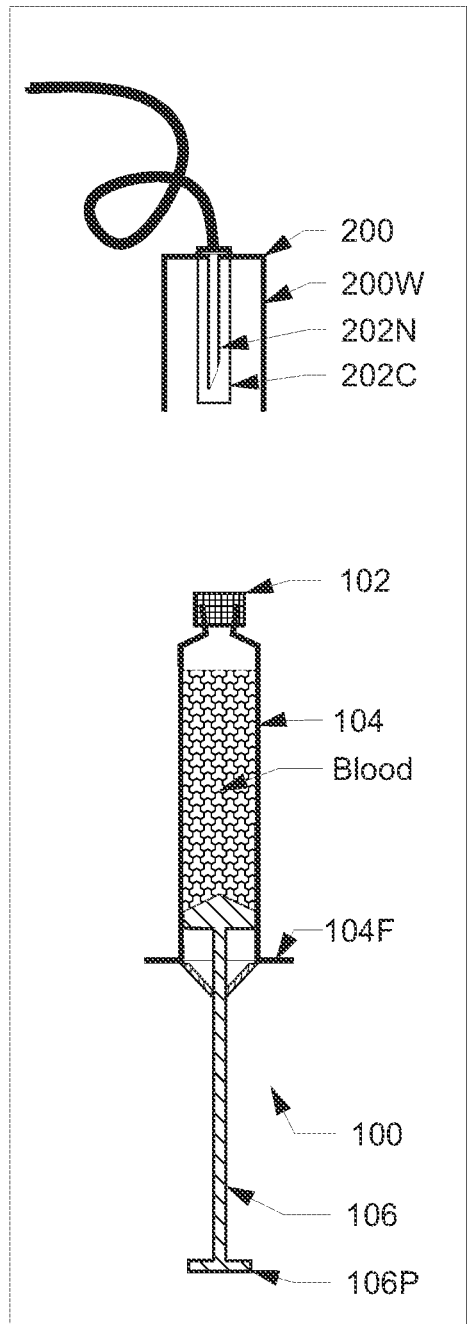
FIGS. 7-9 show the device 100 of FIG. 6 after the blood collection hub is disconnected, after the proximal end of the plunger 106 and tubular member 104 are clipped, and after the device 100 has been centrifuged to separate the blood into plasma, buffy coat, and red blood cells.
Figure 8:
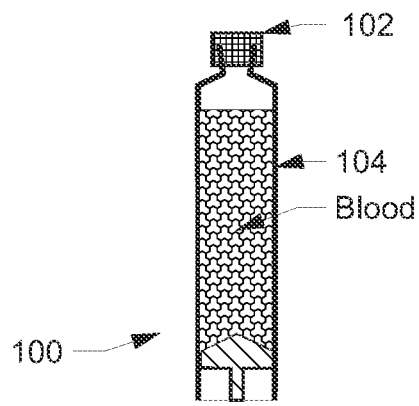

FIGS. 7-8 show the hub assembly 200 being disengaged from the device 100 containing a specimen of blood. Then a proximal portion of the tubular member and a proximal portion of the plunger are cut off (clipped) so that the remaining portion of the syringe-like device 100 will fit into a conventional centrifuge. The proximal portion of the syringe-like device including a proximal end portion of the tubular member 104 and a proximal end portion of the plunger 106 may be cut off using a conventional guillotine or the like cutting device. In some examples, a Syringe Cutter such as disclosed in PCT/US21/43175 filed Jul. 26, 2021 may be used.

Figure 9:
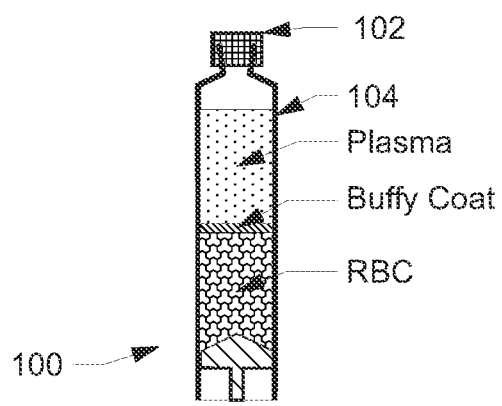

FIG. 9 shows the device 100 of FIG. 8 after being centrifuged thereby separating the blood specimen into its constituent components (plasma, buffy coat and red blood cells (RBC).

Figure 10:
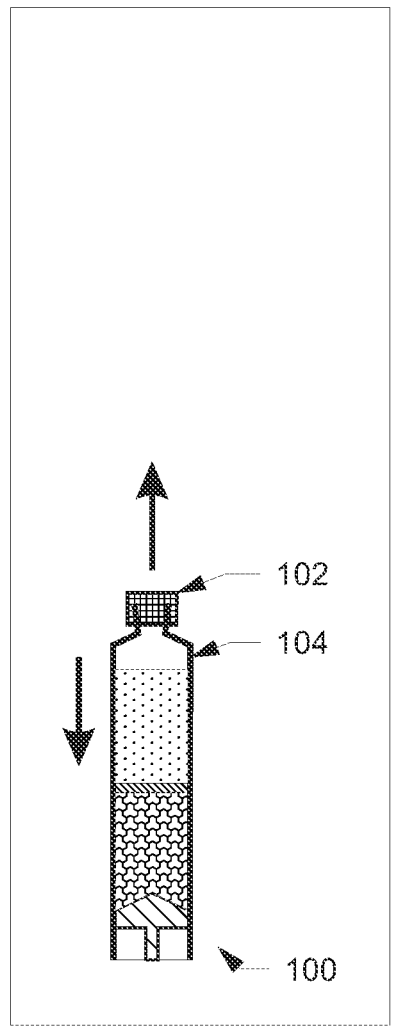
FIGS. 10-11 show the device 100 of FIG. 9 prior to removing the cap 102.

FIG. 10 shows the device 100 of FIG. 9 just before the cap 102 is removed.

Figure 11:
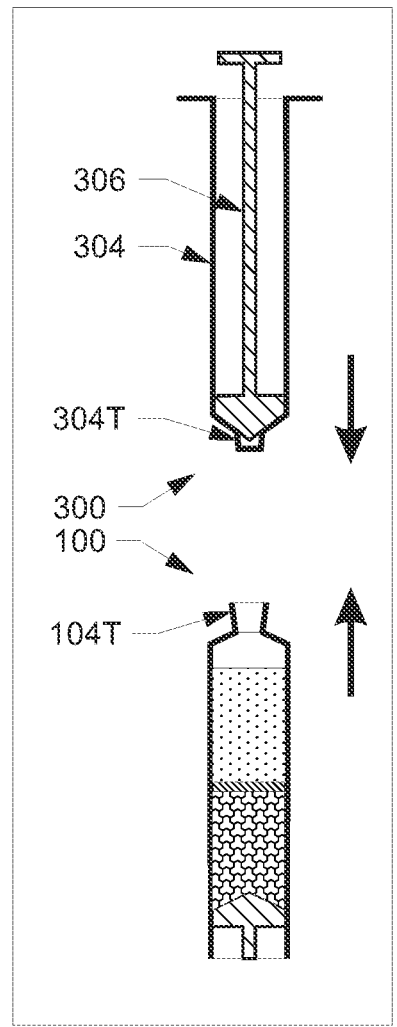
Figure 12:
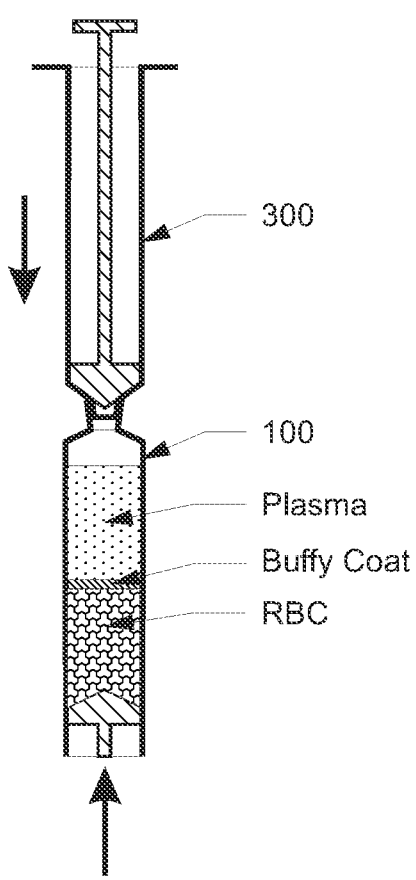
FIGS. 12-13 show the device 100 of FIG. 11 after the device 100 has been coupled to the syringe 300.

FIGS. 11-12, show the device 100 of FIG. 10 being coupled to a conventional syringe 300.

Figure 13:
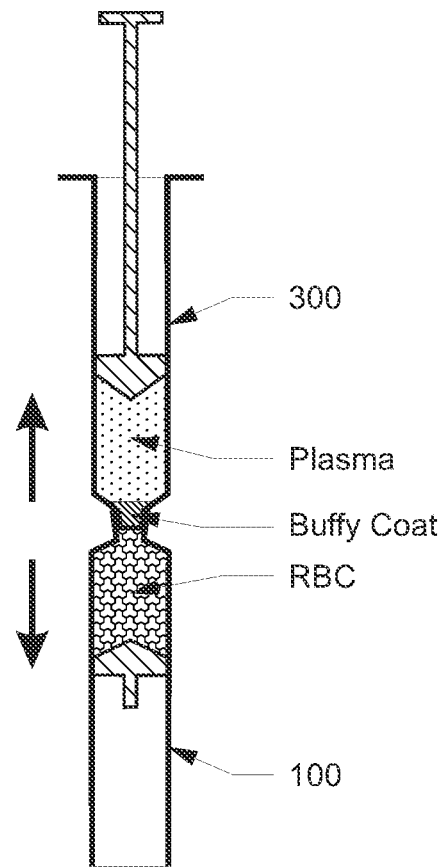

FIG. 13 shows the device 100 of FIG. 12 after the plasma and buffy coat were transferred to the conventional syringe 300.

Figure 14:
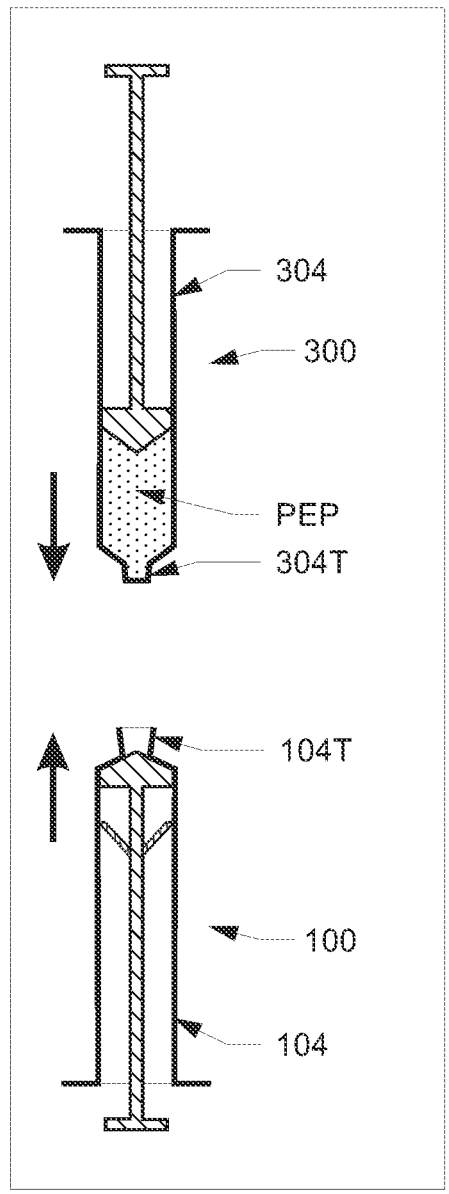
FIGS. 14-15 show the device 300 of FIG. 13 just prior to and after being fluidically coupled with a device 100.
Figure 15:
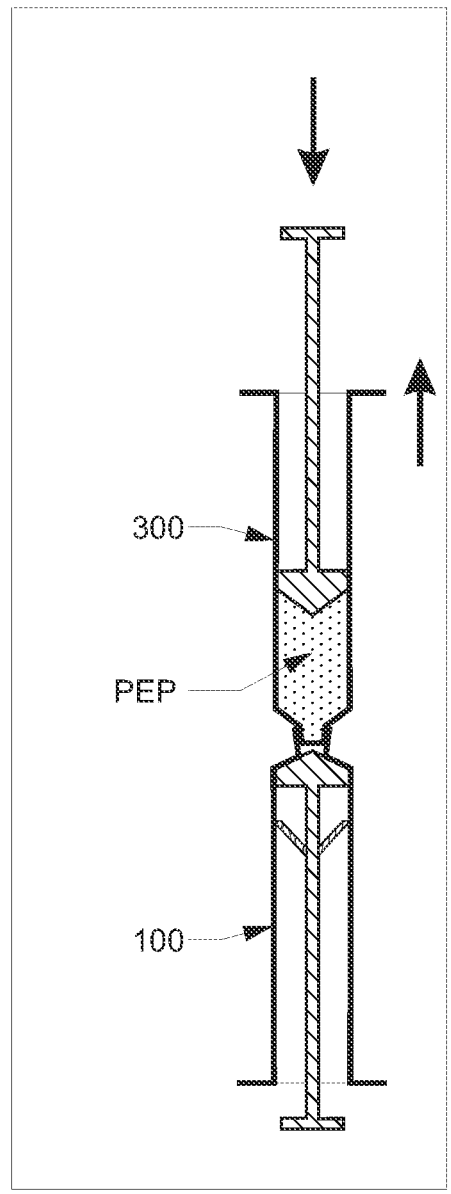

FIGS. 14-15 show the syringe 300 of FIG. 13 being connected to an empty syringe-like device 100.

Figure 16:
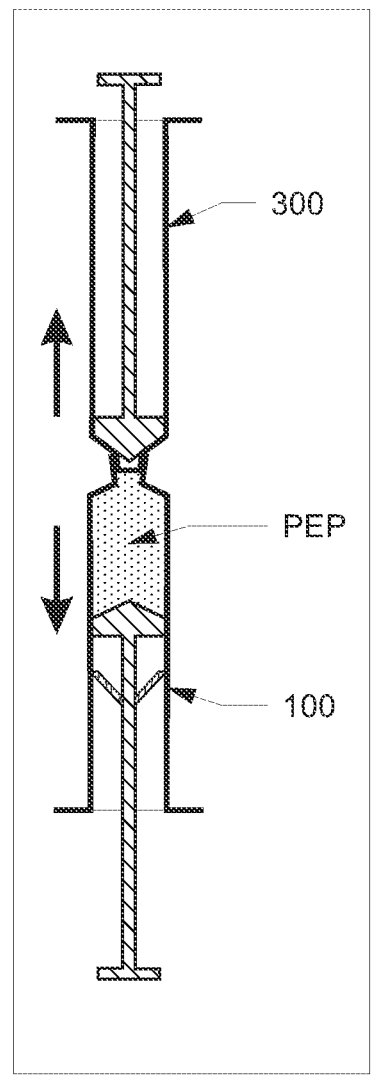
FIG. 16 shows the device 300 of FIG. 15 after the mix of buffy coat and plasma (also known as PEP) has been transferred to the device 100.
Figure 17:
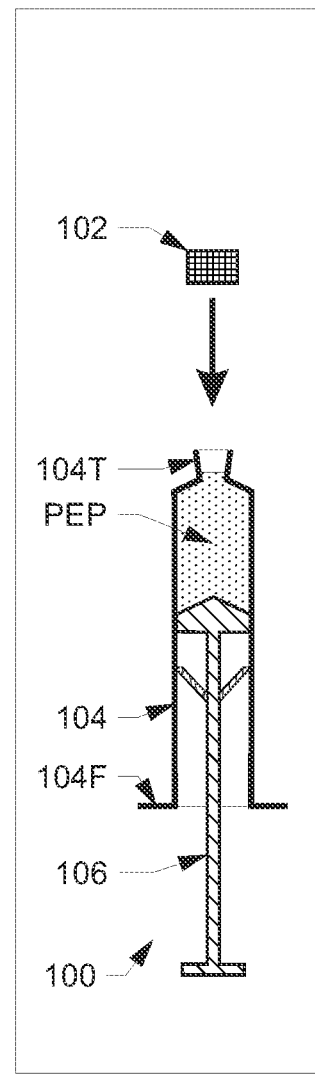
FIG. 17 shows the device 100 of FIG. 16 after it has been disconnected from device 300 and prior to being sealed with cap 102.
Figure 18:
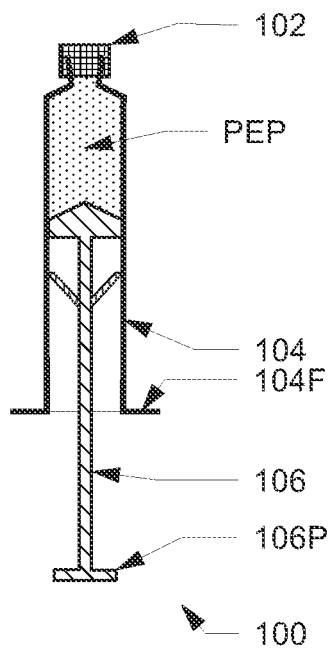
FIGS. 18-19 show the device 100 of FIG. 17 just prior to and after the proximal end of the tubular member and plunger have been clipped.

FIGS. 16-18 show the mixture of plasma and buffy coat (hereinafter termed platelet enriched plasma (PEP)) being transferred from the syringe 300 to the device 100, the empty syringe 300 disconnected and the device 100 now containing PEP being capped with cap 102.

Figure 19:
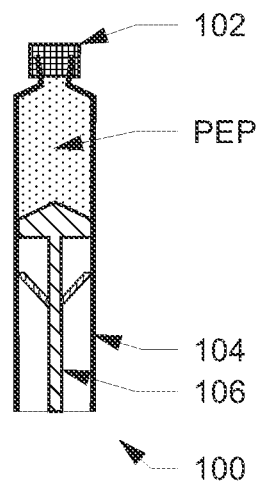

FIG. 19 shows the device 100 of FIG. 18 after the proximal end portion of the syringe-like device 100 is clipped or cut off to facilitate insertion into a centrifuge. More particularly, a proximal end portion of the tubular member 104 (including the flanges) and a proximal end portion of the plunger 106 (including the pad 106P) are clipped or cut off.

Figure 20:
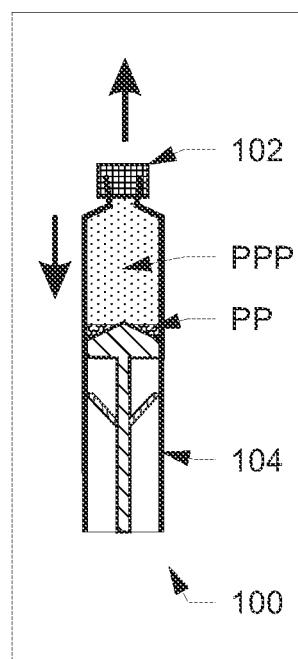
FIG. 20 shows the device 100 of FIG. 19 after it has been centrifuged to separate the PEP into platelet poor plasma (PPP) and platelet pellet (PP)

FIG. 20 shows the device 100 of FIG. 19 after being centrifuged separating the PEP into platelet poor plasma (PPP) and platelet pellet (PP).

Figure 21:
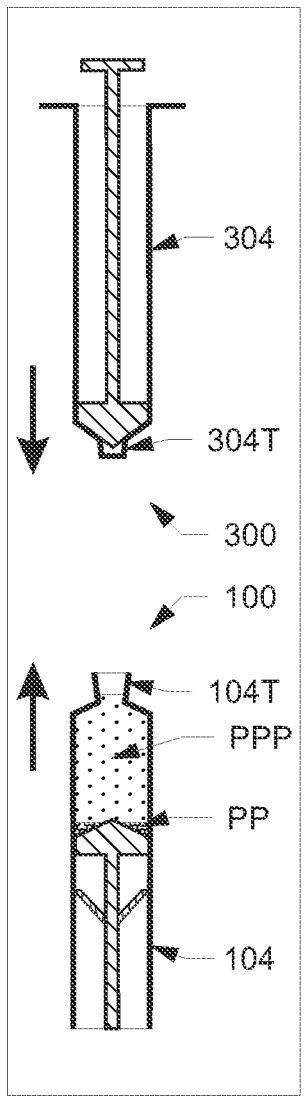
FIGS. 21-22 show the device 100 of FIG. 20 just prior to and after being fluidically coupled with syringe 300.
Figure 22:
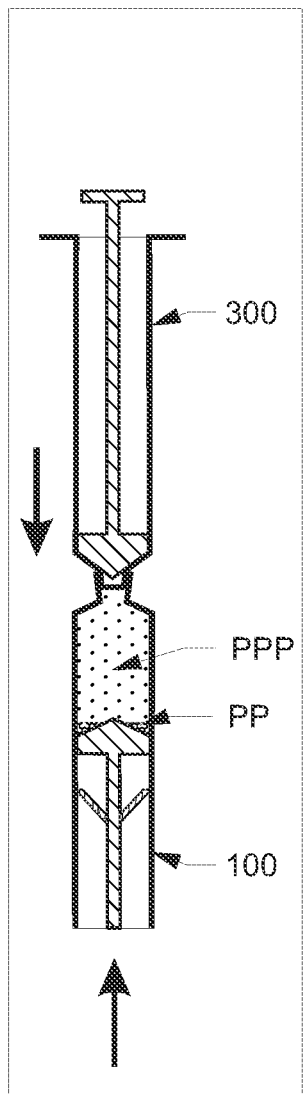
Figure 23:
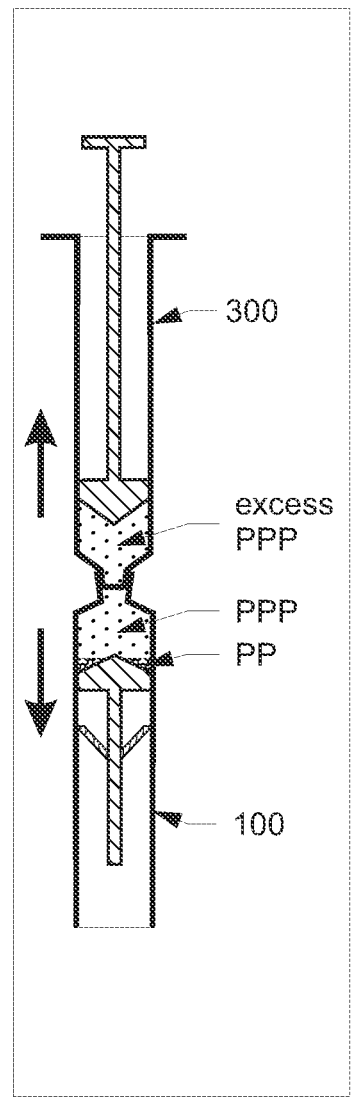
FIG. 23 shows the device 100 of FIG. 22 after a portion of the PPP has been transferred to the syringe 300.

FIGS. 21-23 show the device 100 of FIG. 20, after the cap has been removed, being connected to an empty conventional syringe 300, and a portion, e.g., between ½ to ¾, of the PPP being transferred from the device 100 to the syringe 300.

Figure 24:
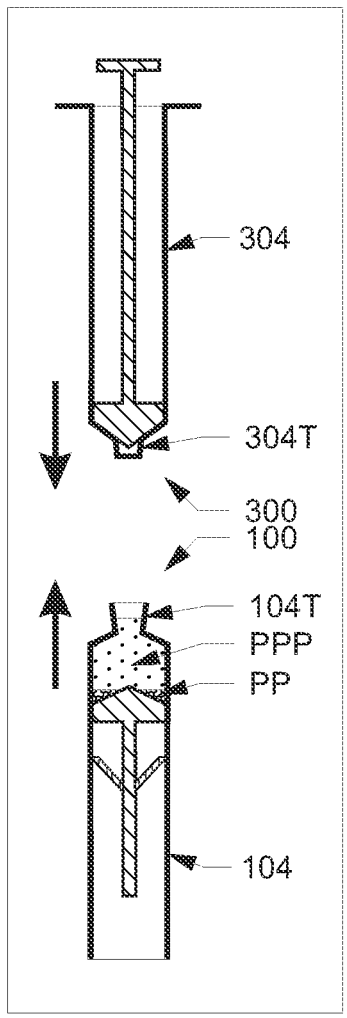
FIGS. 24-25 show the device 100 of FIG. 23 just prior to and after being fluidically coupled with syringe 300.
Figure 25:
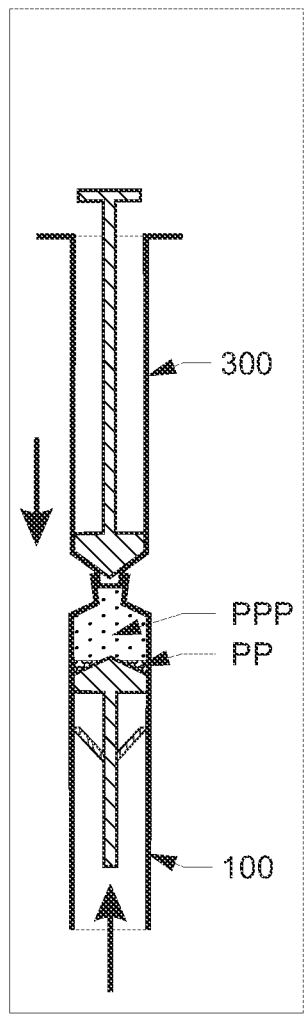
Figure 26:
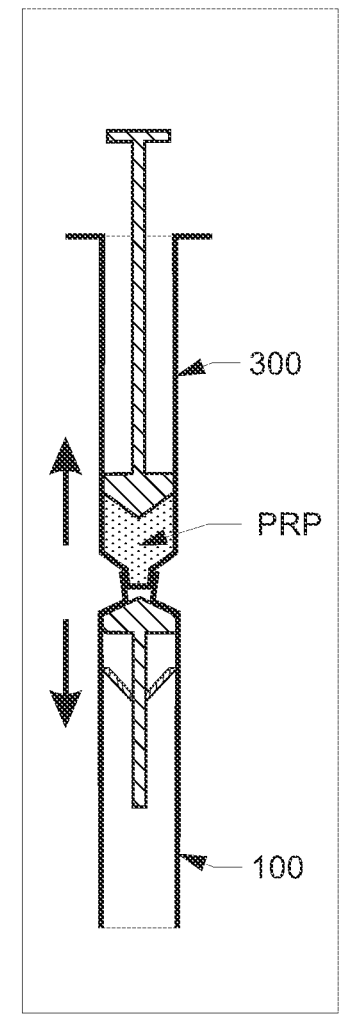
FIG. 26 shows the device 100 of FIG. 25 after the mixture of PP and PPP (also known as platelet rich plasma (PRP)) has been transferred to the syringe 300.

FIGS. 24-26 show the device 100 of FIG. 23 being connected to an empty conventional syringe 300, and the mixture of PPP and PP (hereinafter PRP) being transferred from the device 100 to the syringe 300.

Figure 27:
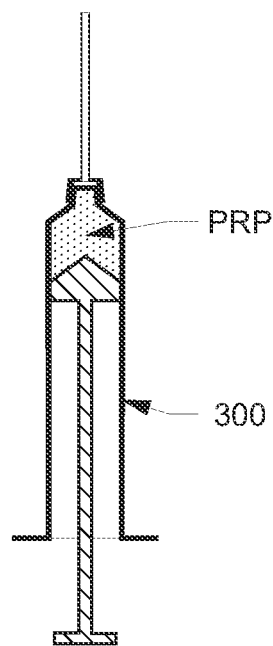
FIG. 27 shows the syringe 300 of FIG. 26 with a needle.

FIG. 27 shows the device 300 from FIG. 26 with a needle attached, ready to inject the PRP.

Figure 34:
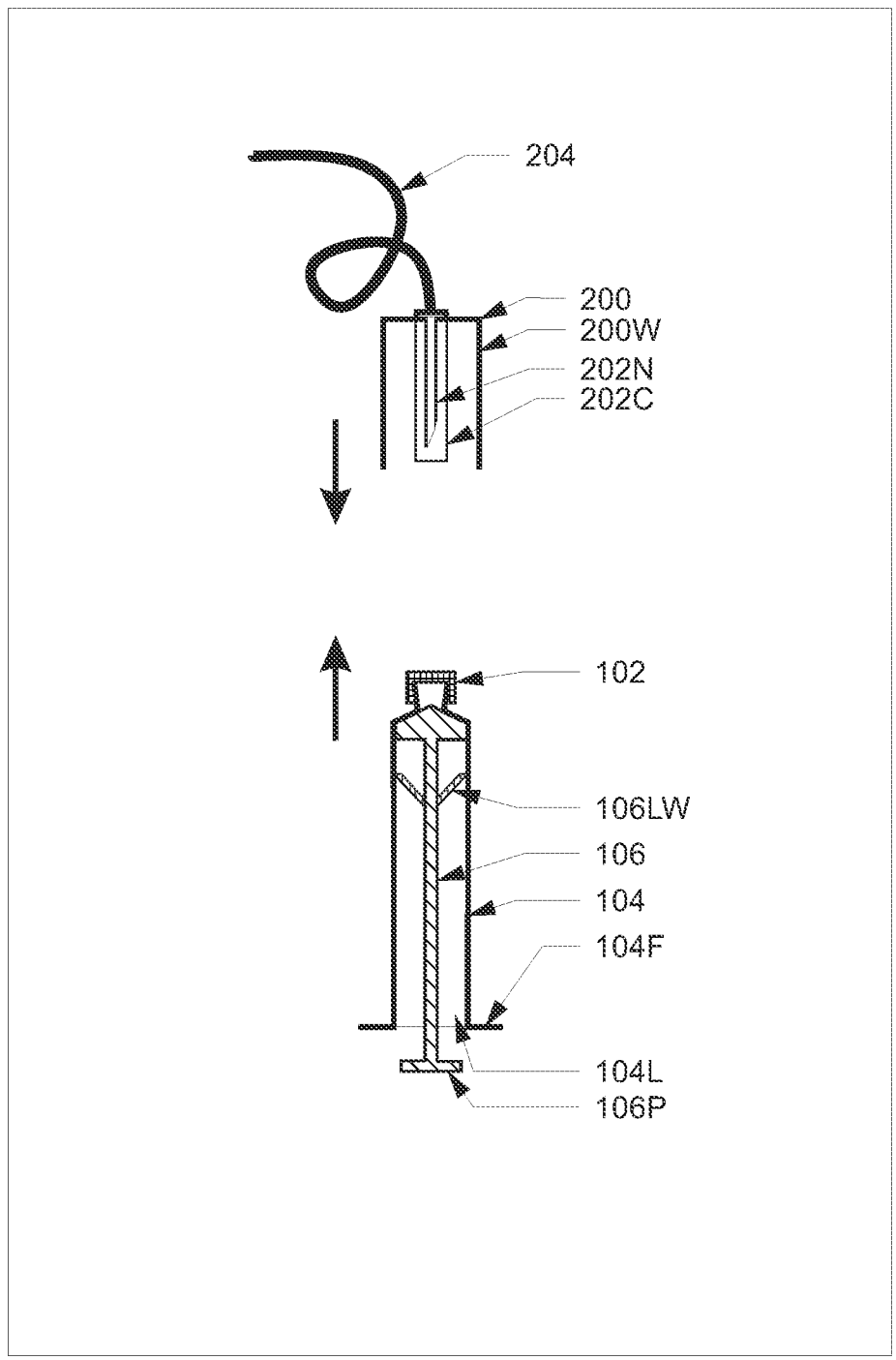
FIGS. 34-35 show the device 100 of FIG. 1 just prior to and after being fluidically coupled with blood collection hub assembly 200.
Figure 35:
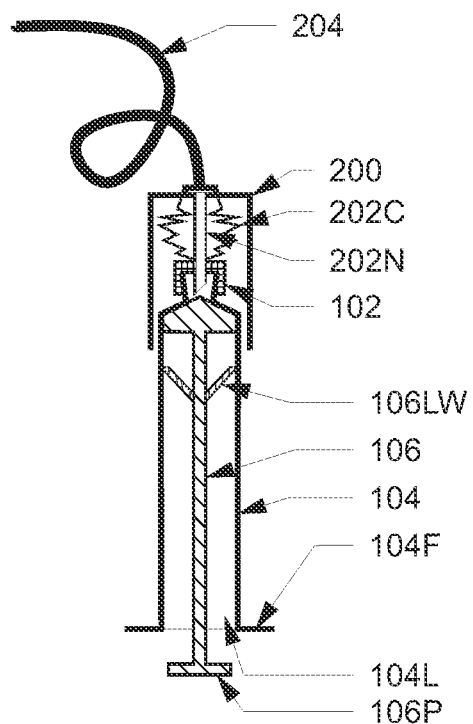
Figure 36:
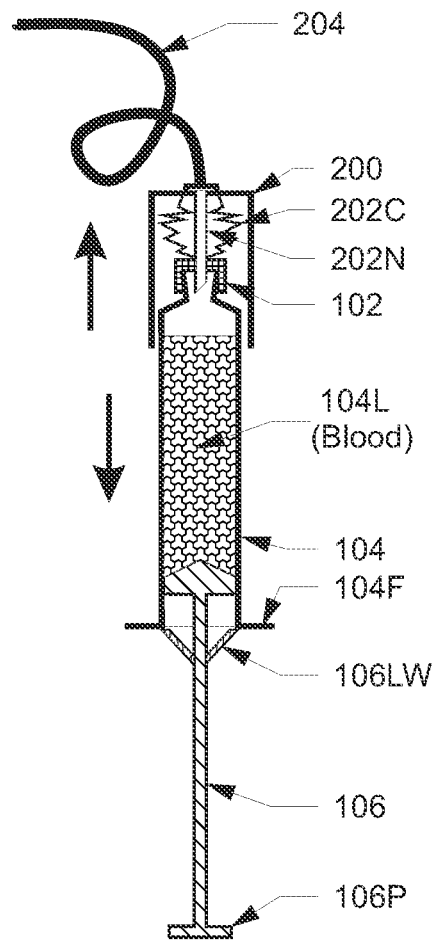
FIG. 36 shows the device 100 of FIG. 35 after the plunger 106 has been retracted proximally, drawing a specimen of blood from the patient through the hub assembly 200 into the interior volume 104L.

FIGS. 1-5 describe a method in which a partial vacuum is created within the interior volume 104L prior to connecting the syringe-like device 100 to the blood collection hub assembly 200, and the partial vacuum is used to draw the blood. In other words, the plunger 106 is retracted (with the cap 102 on) before the device 100 is connected to the hub assembly 200. However, one of ordinary skill in the art will appreciate that the device 100 may be used to collect blood without the need to first create a partial vacuum. According to this example, device 100 as depicted in FIG. 1 with the plunger 106 advanced into the tubular member 104 may be connected to a collection hub assembly 200 (FIGS. 34-35), and then the plunger 106 may be retracted to draw blood into the interior volume 104L (FIG. 36). The locking wing members 106LW provide haptic feedback when they pop-out from the tubular member 104 and engage with the proximal end of the tubular member 104, thereby signaling that the rated capacity of the device 100 has been reached. The rest of the process continues as described above with reference to FIGS. 7-27.

Throughout this disclosure, the conventional syringe 300 has been used to facilitate the transfer from one syringe-like device 100 to another syringe-like device 100. It should be noted that conventional syringes are not approved for use in a centrifuge, thus throughout the process described in this disclosure, only the syringe-like device 100 is used in the centrifuge. There are several reasons to use a conventional syringe 300 to transfer specimens from one syringe-like device 100 to another syringe-like device 100. One reason is that using a conventional syringe 300 to transfer specimens from one syringe-like device 100 to another eliminates the need for an adapter which may be difficult to handle with gloved hands. Another reason is that the cost of the adapter may be greater than the cost of the conventional syringe.

FIGS. 11-16 illustrate the process of transferring platelet enriched plasma (plasma and buffy coat) between two syringe-like devices using a conventional syringe.

A modified process in which the conventional syringe is only used to inject the platelet rich plasma into the patient will now be described. In this example, the method described with respect to FIGS. 1-10 remains the same. The process continues with FIGS. 28-33.

Figure 28:
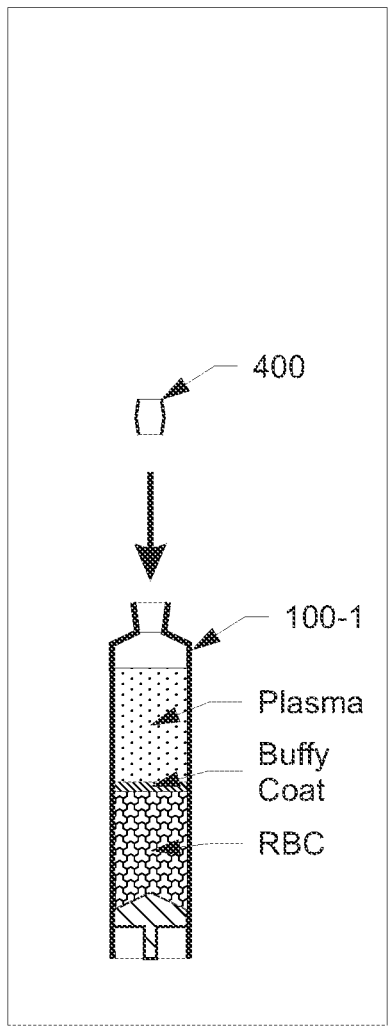
FIG. 28 shows the device 100-1 (100) of FIG. 9 prior to being fluidically coupled with an adapter 400.
Figure 29:
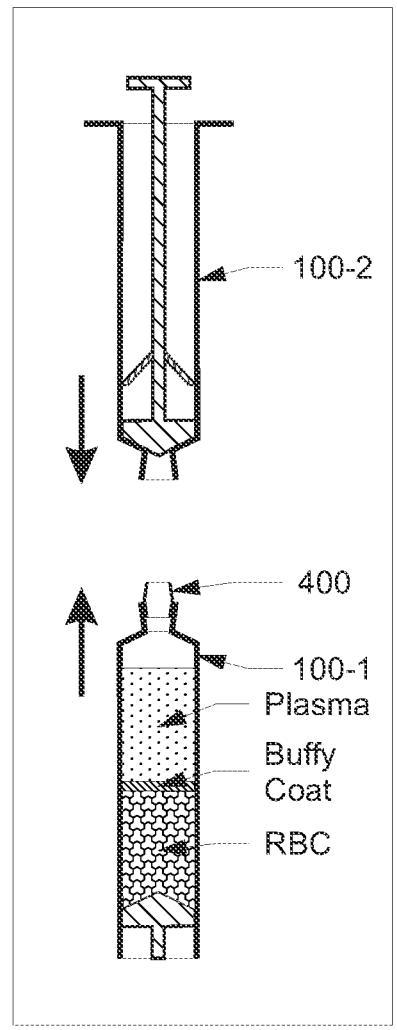
FIGS. 29-30 show the device 100-1 of FIG. 28 prior to and after being fluidically coupled with device 100-2 by adapter 400.
Figure 30:
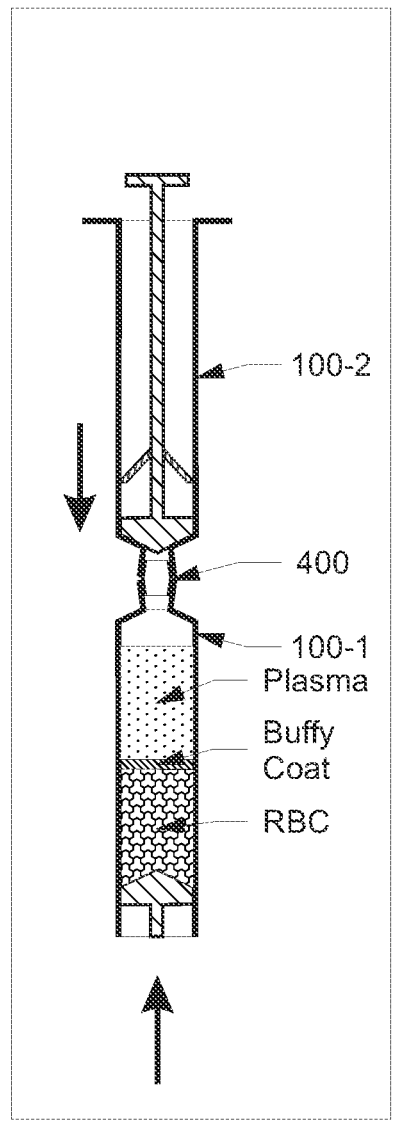

FIGS. 28-30 show the device 100-1 (100) of FIG. 13 being connected to another device 100-2 using an adapter 400.

Figure 31:
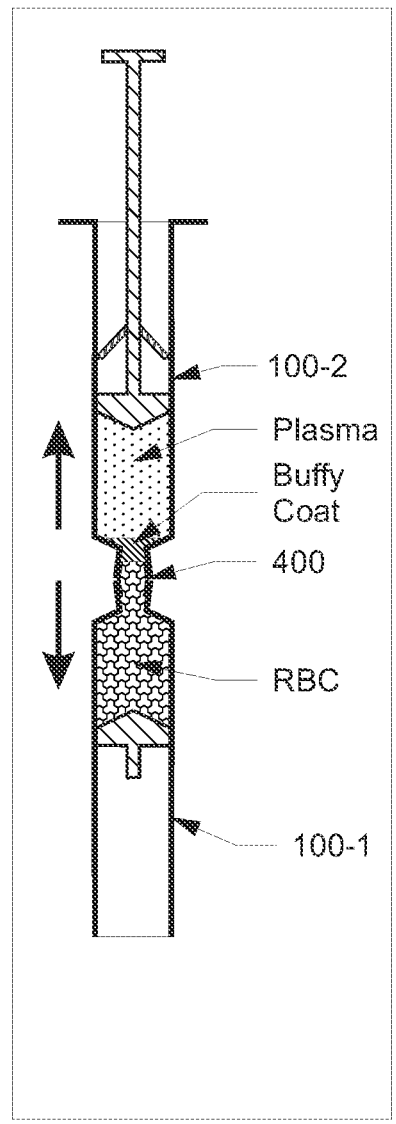
FIG. 31 shows the devices 100-1 and 100-2 of FIG. 29 after the plasma and buffy coat have been transferred to device 100-2.

FIG. 31 shows the device 100-1 of FIG. 30 after the plasma and buffy coat have been transferred to device 100-2.

Figure 32:
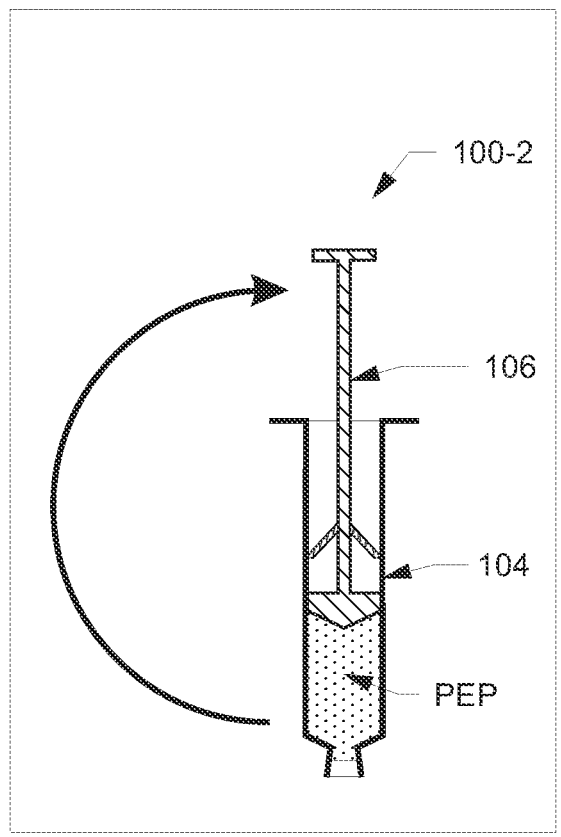
FIG. 32 shows the device 100-2 of FIG. 31 after it has been disconnected from device 100-1.
Figure 33:
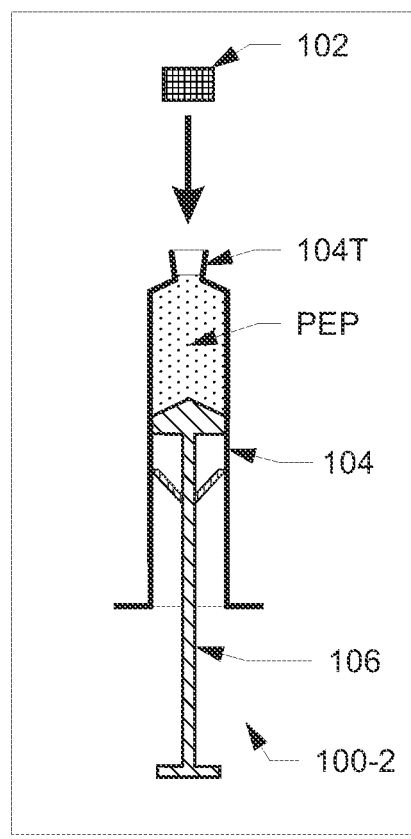
FIG. 33 shows the device 100-2 of FIG. 32 just prior to being sealed with cap 102.

FIGS. 32-33 show the device 100-2 of FIG. 31 after the plasma and buffy coat are mixed to form PEP. The syringe-like device is capped and the rest of the process according to this example continues with FIGS. 18-27. Please note that FIGS. 21-23 depict the use of a conventional syringe but according to this example the conventional syringe 300 is replaced with a syringe-like device 100, and an adapter 400 is used to couple the two syringe-like devices 100-1, 100-2.

The syringe-like device 100 depicted in FIG. 1 includes locking wing members 106LW positioned around a first longitudinal position on the plunger 106. The locking wing members 106LW provide haptic feedback to alert the user when the rated capacity of the device has been reached. Once the locking wing members 106LW engage with the proximal end of the tubular member 104, the plunger 106 is prevented from being moved in a distal direction.

In some examples it may be advantageous to have first and second sets of locking wing members 106LW-1, 106LW-2 at first and second longitudinal positions on the plunger 106. See, FIG. 37. When the plunger 106 is withdrawn a distance X1, the locking wing members 106LW-1 engage with the proximal end of the tubular member 104, the plunger 106 is prevented from being moved in a distal direction. See, FIG. 38. Thereafter, if the plunger 106 is withdrawn a distance X2, the locking wing members 106LW-2 engage with the proximal end of the tubular member 104, the plunger 106 is prevented from being moved in a distal direction.

Figure 37:
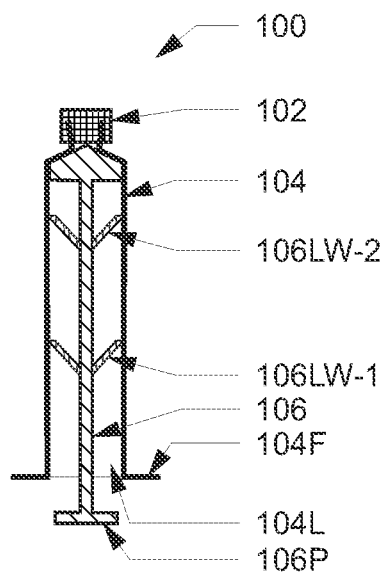
FIG. 37 shows the device 100 with two sets of locking wing members 106LW-1 and 106LW-2 with the plunger 106 fully advanced (distally) into the tubular member 104.

A modified process in which the device 100 of FIG. 37 is used to collect the blood specimen will now be described. In this example, the method begins with FIGS. 37-43 and then continues with the process described with respect to FIGS. 8-27.

FIG. 37 shows the device 100 with the plunger 106 fully advanced into the tubular member 104.

Figure 38:
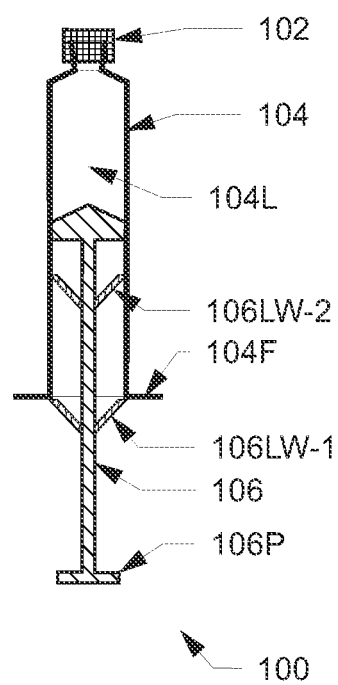
FIG. 38 shows the device 100 of FIG. 37 with the plunger 106 partially retracted (proximally) such the locking wing member 106LW-1 has locked and a partial vacuum created within the interior volume 104L.

FIG. 38 shows the device 100 of FIG. 37 with the plunger 106 retracted (proximally) until locking wing member(s) 106LW-1 engage with the proximal end of the tubular member.

Figure 39:
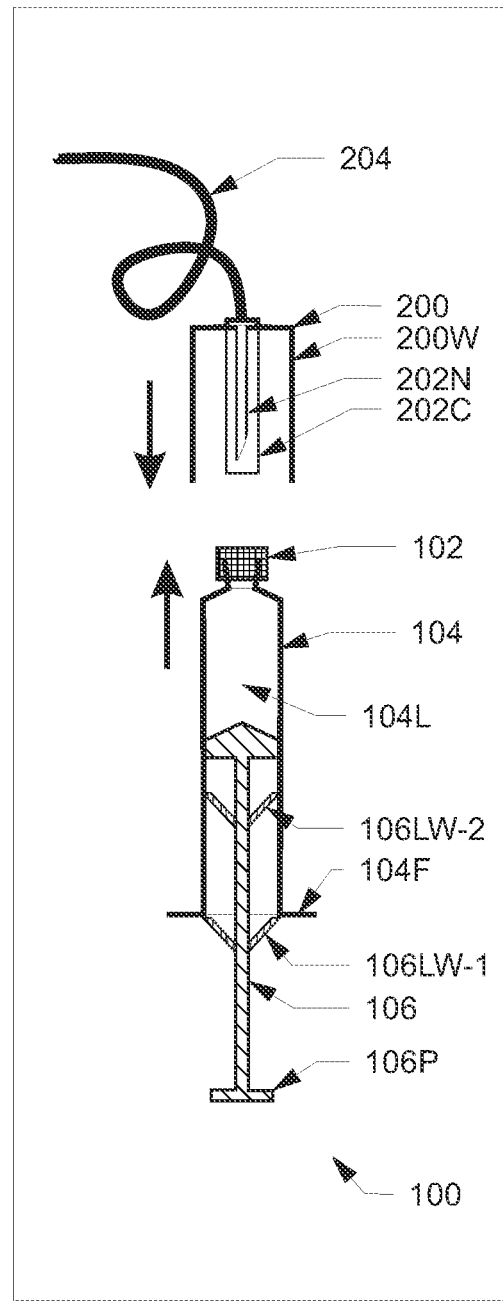
FIG. 39 shows the device 100 of FIG. 38 just prior to being fluidically coupled with blood collection hub assembly 200.

FIGS. 39-40 show the device 100 of FIG. 38 being connected to hub assembly 200.

FIG. 41 shows the device 100 of FIG. 40 after a partial specimen of blood has been transferred into the interior volume 104L.

Figure 42:
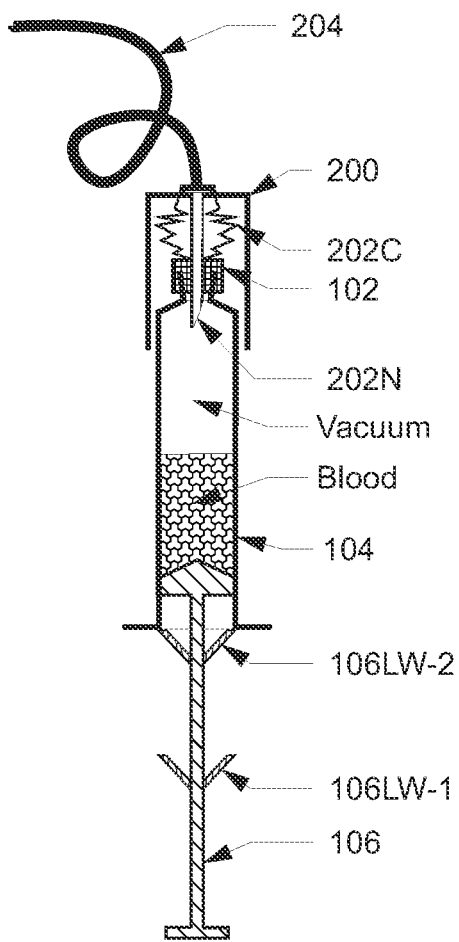
FIG. 42 shows the device 100 of FIG. 41 after the plunger 106 has been withdrawn (proximally) until the locking wing member 106LW-2 has locked and a partial vacuum created within the interior volume 104L.
Figure 43:
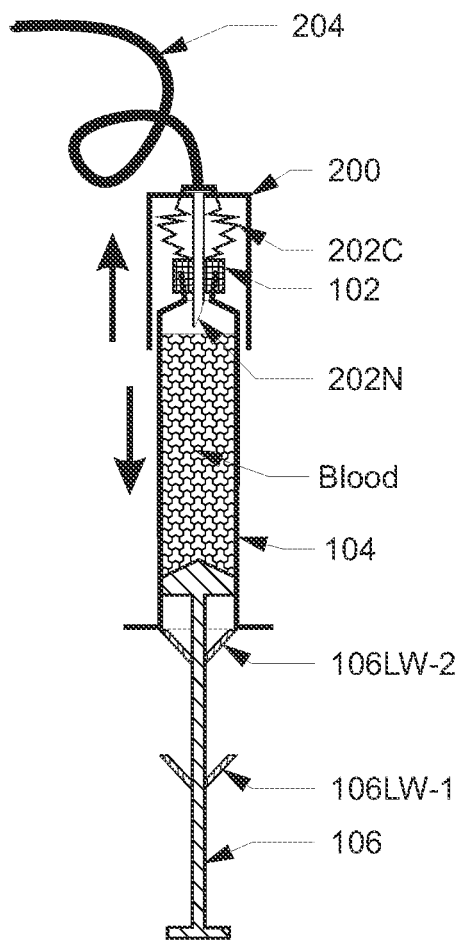
FIG. 43 shows the device 100 of FIG. 42 after an additional specimen of blood has been drawn into the interior volume 104L by the partial vacuum.

FIGS. 42-43 show the device 100 of FIG. 41 after the plunger has been withdrawn proximally until locking wing members 106LW-2 engage with the proximal end of the tubular member, drawing additional blood into the interior volume 104L. The rest of the process continues as described with respect to FIGS. 8-27.

While the present disclosure has been described with reference to various embodiments, these embodiments are illustrative, and the scope of the disclosure is not limited to them. Many variations, modifications, additions, and improvements are possible. More generally, embodiments in accordance with the present disclosure have been described in the context of particular embodiments. Functionality may be separated or combined in procedures differently in various embodiments of the disclosure or described with different terminology. These and other variations, modifications, additions, and improvements may fall within the scope of the disclosure as defined in the claims that follow.

What is claimed:

1. A method for collecting a blood specimen from a patient, comprising the steps of:
   providing a first syringe-like device including:
      a tubular member having a proximal end and a distal end, the tubular member having a diameter D1 enclosing an interior volume, the distal end of the tubular member provided with a tip having a first through-hole in fluid communication with the interior volume, the proximal end of the tubular member having a second through-hole in fluid communication with the interior volume;
      a plunger movably accommodated within the interior volume of the tubular member, the plunger having a proximal end and a distal end, the plunger including an elongate member having an enlarged pad provided on the proximal end of the plunger, an elastomeric member provided on the distal end of the plunger and one or more locking wing members provided on and biased to extend away from the elongate member;
   providing a first cap at least partially formed of a pierceable and self-healing material; providing a blood collection hub assembly including:
      tubing having a first end in fluid communication with a first hollow needle configured to be inserted into a vein of the patient and a second end in fluid communication with a second hollow needle;
      the second hollow needle having a sharpened tip;
      a multisampling safety valve which includes the second hollow needle fully enclosed by a second cap which extends beyond the sharpened tip of the second hollow needle, where the second cap is at least partially formed of a flexible, pierceable and self-healing material which is biased to return to its fully extended shape;
      wherein the multisampling safety valve is closed when the second cap is fully extended and the second hollow needle is enclosed within the second cap, and the multisampling safety valve is open when the second cap is at least partially collapsed such that the second hollow needle pierces through the second cap; and
      a wall encircling the second hollow needle and the second cap and having a diameter D2 slightly larger than D1 and configured to align an axis of the second hollow needle with an axis of the first through-hole when the blood collection hub assembly is placed in engagement with the tubular member;
   placing the first cap on the tip of the tubular member of the first syringe-like device with the plunger fully inserted into the tubular member such that the distal end of the plunger is proximate the distal end of the tubular member;
   retracting the plunger proximally thereby creating a partial vacuum within the interior volume of the tubular member; and
   placing the blood collection hub assembly in engagement with the capped tip of the tubular member of the first syringe-like device such that the second hollow needle pierces the second cap and the first cap;
   wherein the specimen of blood is configured to be drawn from the patient, through the first hollow needle, the tubing, the second hollow needle, and into the interior volume of the tubular member of the first syringe-like device by the partial vacuum within the interior volume of the tubular member.

2. The method of claim 1, comprising:
   disengaging the blood collection hub assembly from the first syringe-like device;
   clipping the proximal end of the tubular member and the proximal end of the plunger of the first syringe-like device; and
   centrifuging the first syringe-like device to separate the blood specimen into plasma, buffy coat and red blood cells (RBC).

3. The method of claim 2, comprising:
   providing a first conventional syringe having at least partially inserted plunger;
   removing the first cap from the tip of the tubular member of the first syringe-like device;
   fluidically coupling a tip of the first conventional syringe with the tip of the tubular member of the first syringe-like device and transferring the plasma and the buffy coat into the first conventional syringe; and
   disconnecting the first conventional syringe from the first syringe-like device.

4. The method of claim 3, comprising;
   providing a second syringe-like device including:
   a tubular member having a proximal end and a distal end, the tubular member having a diameter D1 enclosing an interior volume, the distal end of the tubular member provided with a tip having a first through-hole in fluid communication with the interior volume, the proximal end of the tubular member having a second through-hole in fluid communication with the interior volume, said tubular member having a plunger at least partially inserted;
   fluidically coupling the tip of the first conventional syringe with the tip of the tubular member of the second syringe-like device and transferring the plasma and buffy coat from the first conventional syringe into the second syringe-like device;
   disconnecting the first conventional syringe from the second syringe-like device;
   setting aside the first conventional syringe;
   placing the first cap on the tip of the tubular member of the second syringe-like device;
   clipping the proximal end of tubular member and a proximal portion of the plunger of the second syringe-like device; and
   centrifuging the second syringe-like device to yield a layer of platelets and a layer of platelet poor plasma.

5. The method of claim 4, comprising:
   providing a second conventional syringe or reusing the first conventional syringe;
   removing the first cap from the tip of the tubular member of the second syringe-like device;
   fluidically coupling the tip of the first conventional syringe or the tip of the second conventional syringe with the tip of the tubular member of the second syringe-like device and transferring a portion of the platelet poor plasma into the first or second conventional syringe;
   disconnecting the first or second conventional syringe from the second syringe-like device; and
   setting aside the first or second conventional syringe.

6. The method of claim 5, comprising:
providing a third conventional syringe or reusing the first conventional syringe or the second conventional syringe; and
fluidically coupling the tip of the first, or second conventional syringes, or a tip of the third conventional syringes with the tip of the tubular member of the second syringe-like device and transferring the platelets with the platelet-poor plasma from the second syringe-like device into the first, second, or third conventional syringes.

7. A device for collecting blood, comprising:
a tubular member having a diameter D1 enclosing an interior volume having a rated capacity, a distal end of the tubular member provided with a tip having a first through-hole in fluid communication with the interior volume, a proximal end of the tubular member provided a second through-hole in fluid communication with the interior volume;
a cap at least partially formed of a pierceable and self-healing material and configured to seal the tip of the tubular member; and
a plunger movably accommodated within the interior volume of the tubular member, the plunger including an elongate member having an enlarged pad provided on a proximal end, an elastomeric member provided on a distal end and one or more locking wing members provided on and biased to extend away from the elongate member;
wherein when the plunger is retracted to the rated capacity, the one or more locking wing members extend beyond the interior volume and engage with the proximal end of the tubular member.

8. The device of claim 7, wherein the one or more locking wing members provide haptic feedback when they engage with the proximal end of the tubular member.

9. The device of claim 7, wherein the one or more locking wing members provide an audible sound when they engage with the proximal end of the tubular member.

10. The device of claim 7, wherein the cap engages and seals the first through-hole.

11. The device of claim 7, wherein when the cap is placed in engagement with the tip of the tubular member after the plunger is at least partially inserted into the tubular member, and then the plunger is retracted, a partial vacuum is created within the interior volume of the tubular member.

12. The device of claim 7 wherein the one or more locking wing members comprise a first set of locking wing members provided a distance X1 from the proximal end of elongate member and a second set of locking wing members provided a distance X2 from the proximal end of elongate member wherein X1<X2.

13. The device of claim 12, wherein the distance X1 and X2 each determines the interior volume within the tubular member and is defined by a position of the distal end of the plunger within the tubular member; and
wherein X1, X2 each defines a trigger point at which each set of locking wing members will lock the plunger.

14. The device of claim 7, wherein the capped tip of the tubular member is configured to sealingly engage and fluidically connect with a needle of a multisampling safety valve of a blood collection hub assembly.

15. The device of claim 14, wherein the cap and the tip of the tubular member are configured to operatively engage with the multisampling safety valve of the blood collection hub assembly.

16. The device of claim 15, wherein the blood collection hub assembly includes a circular wall having a diameter which is sized to accommodate the distal end of the tubular member, and wherein an interaction between the circular wall and the distal end of the tubular member orients the needle with respect to the cap to facilitate insertion of the needle through the cap.

17. The device of claim 15, wherein the blood collection hub assembly includes a circular wall having a diameter which is sized to accommodate a capped tip of the tubular member, and wherein an interaction between the circular wall and the tubular member orients the needle with respect to the cap to facilitate insertion of the needle through the cap.

18. A method for collecting a blood specimen from a patient into a syringe-like device, comprising the steps of:
providing a first syringe-like device including:
a tubular member having a proximal end and a distal end, the tubular member having a diameter D1 enclosing an interior volume, the distal end of the tubular member provided with a tip having a first through-hole in fluid communication with the interior volume, the proximal end of the tubular member provided a second through-hole in fluid communication with the interior volume;
a plunger movably accommodated within the interior volume of the tubular member, the plunger including an elongate member having an enlarged pad provided on a proximal end, an elastomeric member provided on distal end and one or more locking wing members provided on and biased to extend away from the elongate member;
providing a first cap at least partially formed of a pierceable and self-healing material;
providing a blood collection hub assembly including:
tubing having a first end in fluid communication with a first hollow needle configured to be inserted into a vein of the patient and a second end in fluid communication with a second hollow needle;
the second hollow needle having a sharpened tip;
a multisampling safety valve which includes the second hollow needle fully enclosed by a second cap which extends beyond the sharpened tip of the second hollow needle, where the second cap is at least partially formed of a flexible, pierceable and self-healing material which is biased to return to its fully extended shape;
wherein the multisampling safety valve is closed when the second cap is fully extended and the second hollow needle is enclosed within the second cap, and the multisampling safety valve is open when the second cap 1s at least partially collapsed such that the second hollow needle pierces the second cap; and
a wall encircling the second hollow needle and the second cap, the wall having a diameter D2 slightly larger than D1 and configured to align an axis of the second hollow needle with an axis of the first through-hole when the blood collection hub assembly is placed in engagement with the tubular member; inserting the first hollow needle into the vein of the patient;
placing the first cap on the tip of the tubular member of the first syringe-like device with the plunger fully inserted into the tubular member such that the distal end of the plunger is proximate the distal end of the tubular member; placing the blood collection hub assembly in engagement with the capped tip of the tubular member of the first syringe-like device such that the second hollow needle pierces the second cap and the first cap; and retracting the plunger proximally thereby drawing the specimen of blood from the patient, through the first hollow needle, the tubing; the second hollow needle, into the interior volume of the tubular member of the first syringe-like device by a partial vacuum within the interior volume of the tubular member.

19. The method of claim 18, comprising:
disengaging the blood collection hub assembly from the first syringe-like device;
clipping the proximal end of tubular member and the proximal end of the plunger of the first syringe-like device; and
centrifuging the first syringe-like device to separate the blood specimen into plasma, buffy coat and red blood cells (RBC).

20. The method of claim 19, comprising:
providing a conventional syringe having at least partially inserted plunger;
removing the first cap from the tip of the first syringe-like device;
fluidically coupling a tip of the conventional syringe with the tip of the first syringe-like device and transferring the plasma and the buffy coat into the conventional syringe; and
disconnecting the conventional syringe from the first syringe-like device.

21. The method of claim 20, comprising:
providing a second syringe-like device including:
a tubular member having a proximal end and a distal end, the tubular member having a diameter D1 enclosing an interior volume, the distal end of the tubular member provided with a tip having a first through-hole in fluid communication with the interior volume, the proximal end of the tubular member provided a second through-hole in fluid communication with the interior volume;
a plunger having a proximal end and a distal end, the plunger movably accommodated within the interior volume of the tubular member, the plunger including an elongate member having an enlarged pad provided on the proximal end, an elastomeric member provided on the distal end and one or more locking wing members provided on and biased to extend away from the elongate member;
fluidically coupling the tip of the conventional syringe with the tip of the second syringe-like device and transferring the plasma and buffy coat into the second syringe-like device;
disconnecting the conventional syringe from the second syringe-like device;
setting aside the conventional syringe;
placing the first cap on the tip of the second syringe-like device;
clipping the proximal end of tubular member of the second syringe-like device and clipping the proximal end of the plunger of the second syringe-like device; and
centrifuging the second syringe-like device to yield a layer of platelets and a layer of platelet poor plasma.

22. The method of claim 21, comprising:
providing a second conventional syringe;
removing the first cap from the tip of the second syringe-like device;
fluidically coupling a tip of the second conventional syringe with the tip of the second syringe-like device and transferring a portion of the platelet poor plasma into the second conventional syringe; and
disconnecting the second conventional syringe from the second syringe-like device.

23. The method of claim 22, comprising:
providing a third conventional syringe;
fluidically coupling a tip of the third conventional syringe with the tip of the second syringe-like device and transferring the platelets with the platelet-poor plasma into the third conventional syringe; and
disconnecting the third conventional syringe from the second syringe-like device.

24. The method of claim 19, comprising:
providing a second syringe-like device, the second syringe-like device having:
a tubular member having a proximal end and a distal end, the tubular member having a diameter D1 enclosing an interior volume, the distal end of the tubular member provided with a tip having a first through-hole in fluid communication with the interior volume, the proximal end of the tubular member having a second through-hole in fluid communication with the interior volume, the tubular member having an at least partially inserted plunger;
removing the first cap from the tip of the first syringe-like device;
fluidically coupling a tip of the second syringe-like device with the tip of the first syringe-like device using an adapter and transferring the plasma and the buffy coat into the second syringe-like device; and
disconnecting the second syringe-like device from the first syringe-like device.

25. The method of claim 24, comprising;
removing the adapter from the tip of the second syringe-like device;
placing the first cap on the tip of the second syringe-like device;
clipping the proximal end of tubular member and the proximal end of the plunger of the second syringe-like device; and
centrifuging the second syringe-like device to yield a layer of platelets and a layer of platelet poor plasma.

26. The method of claim 25, comprising:
providing a first conventional syringe;
removing the first cap from the second syringe-like device;
fluidically coupling the tip of the tubular member of the second syringe-like device with a tip of the first conventional syringe, and transferring a portion of the platelet poor plasma into the first conventional syringe; and
disconnecting the first conventional syringe from the second syringe-like device.

27. The method of claim 26, further comprising the step of
providing a second conventional syringe; and
fluidically coupling a tip of the second conventional syringe with the tip of the second syringe-like device and transferring the platelets with platelet-poor plasma into the second conventional syringe.

28. A method for collecting a blood specimen from a patient, comprising the steps of:
providing a first syringe-like device including:
a tubular member having a proximal end and a distal end, the tubular member having a diameter D1 enclosing an interior volume, the distal end of the tubular member provided with a tip having a first through-hole in fluid communication with the interior volume, the proximal end of the tubular member having a second through-hole in fluid communication with the interior volume;

a plunger having a proximal end and a distal end, the plunger movably accommodated within the interior volume of the tubular member, the plunger including an elongate member having an enlarged pad provided on the proximal end of the plunger, an elastomeric member provided on the distal end of the plunger;

providing a first cap at least partially formed of a pierceable and self-healing material;

providing a blood collection hub assembly including:

tubing having a first end in fluid communication with a first hollow needle configured to be inserted into a vein of the patient and a second end in fluid communication with a second hollow needle;

a multisampling safety valve which includes the second hollow needle fully enclosed by a second cap, wherein the multisampling safety valve is closed when the second needle is disengaged from the second cap and the first cap, and the multisampling safety valve is open when the second hollow needle is engaged with the second cap and the first cap;

placing the first cap on the tip of the tubular member of the first syringe-like device with plunger fully inserted into the tubular member such that the distal end of the plunger is proximate the distal end of the tubular member;

inserting the first hollow needle into the vein of the patient; and placing the blood collection hub assembly in engagement with the capped tip of the tubular member of the first syringe-like device such that the second hollow needle pierces the second cap and the first cap.

29. The method of claim 28, further comprising:

providing means for selectively preventing the plunger from advancing into the tubular member;

wherein prior to or after the step of placing the blood collection hub assembly in engagement with the capped tip of the tubular member of the first syringe-like device, retracting the plunger proximally thereby creating a partial vacuum within the interior volume of the tubular member; and engaging said means for selectively preventing the plunger from advancing into the tubular member;

wherein the specimen of blood is drawn from the patient, through the first hollow needle, the tubing, the second hollow needle, and into the interior volume of the tubular member of the first syringe-like device by the partial vacuum within the interior volume of the tubular member.

* * * * *